United States Patent
Ishihara et al.

(10) Patent No.: US 9,642,596 B2
(45) Date of Patent: May 9, 2017

(54) ULTRASOUND IMAGING APPARATUS

(75) Inventors: Chizue Ishihara, Tokyo (JP); Kunio Hashiba, Tokyo (JP); Hiroki Tanaka, Tokyo (JP); Akifumi Sako, Tokyo (JP); Tomoko Takenaka, Tokyo (JP)

(73) Assignee: HITACHI, LTD., Tokyo (JP)

( * ) Notice: Subject to any disclaimer, the term of this patent is extended or adjusted under 35 U.S.C. 154(b) by 535 days.

(21) Appl. No.: 13/985,122

(22) PCT Filed: Jan. 20, 2012

(86) PCT No.: PCT/JP2012/051259
§ 371 (c)(1),
(2), (4) Date: Aug. 13, 2013

(87) PCT Pub. No.: WO2012/144243
PCT Pub. Date: Oct. 26, 2012

(65) Prior Publication Data
US 2013/0331699 A1 Dec. 12, 2013

(30) Foreign Application Priority Data

Apr. 20, 2011 (JP) .................................. 2011-094418

(51) Int. Cl.
*A61B 8/00* (2006.01)
*A61B 8/14* (2006.01)
(Continued)

(52) U.S. Cl.
CPC .................. *A61B 8/14* (2013.01); *A61B 8/48* (2013.01); *A61B 8/5207* (2013.01); *A61B 8/54* (2013.01);
(Continued)

(58) Field of Classification Search
CPC .... A61B 8/14; A61B 8/48; A61B 8/54; A61B 8/5207; A61B 8/4483; A61B 8/4488;
(Continued)

(56) References Cited

U.S. PATENT DOCUMENTS 5,577,505 A 11/1996 Brock-Fisher et al.
5,678,553 A 10/1997 Uhlendorf et al.
(Continued)

FOREIGN PATENT DOCUMENTS

CN 101347345 1/2009
JP 11000328 1/1999
(Continued)

OTHER PUBLICATIONS

Foreign Office Action.
International Search Report issued in corresponding application No. PCT/JP2012/051259 on Apr. 24, 2012.

*Primary Examiner* — Elmer Chao
(74) *Attorney, Agent, or Firm* — Brundidge & Stanger, P.C.

(57) ABSTRACT

Even when electroacoustic conversion elements with high nonlinearity are employed, a nonlinear imaging is carried out with extracting more nonlinear components. An ultrasonic wave beam is transmitted twice from the transmitter to an identical position on the imaging target, and the signal processor performs computation on the reception signals obtained in every transmission performed twice, thereby extracting a nonlinear component included in the reception signals. In one transmission out of the transmission performed twice, the transmitter delivers the transmission signal to all of multiple electroacoustic conversion elements for driving the electroacoustic conversion elements, and in the other transmission, the transmission signal is delivered selectively only to a part of the multiple electroacoustic conversion elements for driving the electroacoustic conversion elements.

21 Claims, 18 Drawing Sheets

(51) Int. Cl.
*A61B 8/08* (2006.01)
*G01S 7/52* (2006.01)
*G01S 15/89* (2006.01)

(52) U.S. Cl.
CPC ...... *G01S 7/52038* (2013.01); *G01S 7/52047* (2013.01); *G01S 15/8927* (2013.01)

(58) Field of Classification Search
CPC . A61B 8/5246; A61B 8/5269; G01S 7/52038; G01S 7/52047; G01S 15/8927
See application file for complete search history.

(56) References Cited

U.S. PATENT DOCUMENTS

| | | | |
|---|---|---|---|
| 6,095,980 A | 8/2000 | Burns et al. | |
| 7,589,455 B2 | 9/2009 | Adachi et al. | |
| 2005/0256404 A1 | 11/2005 | Sato | |
| 2007/0242567 A1* | 10/2007 | Daft | A61B 8/12 367/140 |
| 2009/0024036 A1 | 1/2009 | Pan et al. | |
| 2012/0296215 A1* | 11/2012 | Brown | A61B 8/5269 600/447 |

FOREIGN PATENT DOCUMENTS

| | | |
|---|---|---|
| JP | 11318889 | 11/1999 |
| JP | 2005319177 A | 11/2005 |
| JP | 2009-18161 A | 1/2009 |
| JP | 2009018161 | 1/2009 |
| WO | 2006129525 | 5/2012 |

\* cited by examiner

FIG. 5
(A)
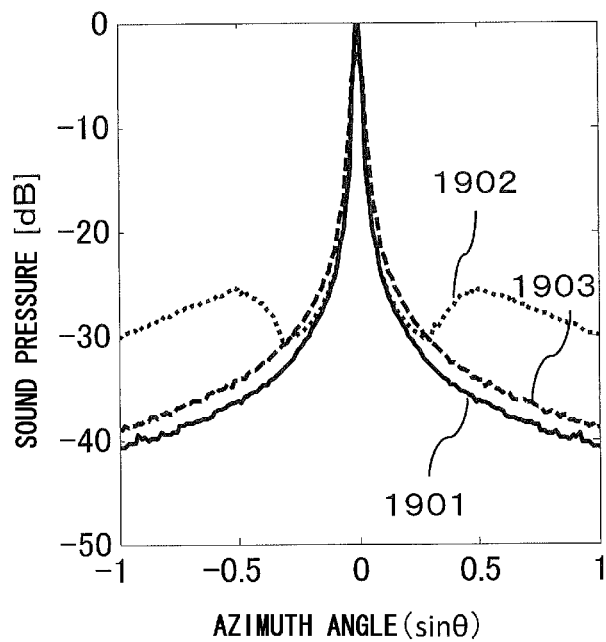
(B)
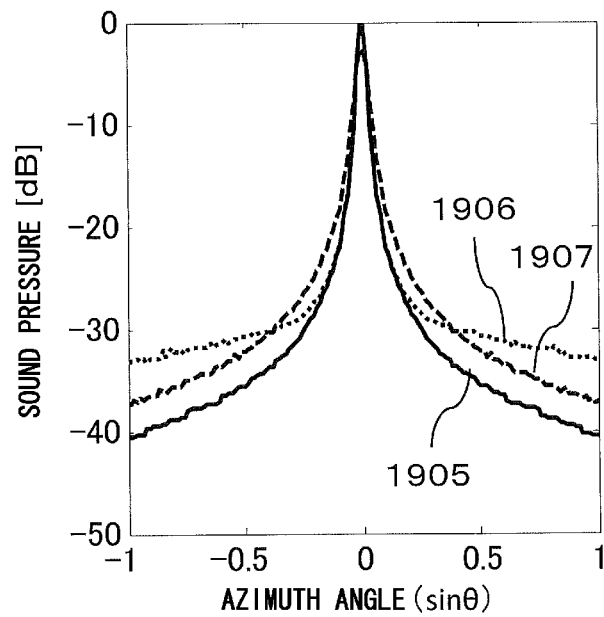

FIG. 6

| WAVE NUMBER (FRACTIONAL BANDWIDTH) | | 1 | | | | 2 | | | |
|---|---|---|---|---|---|---|---|---|---|
| $\lambda/d$ | | 0.5 | 1.0 | 1.5 | 2.0 | 0.5 | 1.0 | 1.5 | 2.0 |
| FOCUS DEPTH [mm] | 5 | A | A | A | N | N | N | N | N |
| | 10 | A | A | A | A | A | A | B | N |
| | 20 | A | A | A | B | A | A | B | B |
| | 30 | A | A | A | B | A | A | B | B |

$\lambda$: WAVELENGTH (= SOUND VELOCITY/FREQUENCY)
d: DISTANCE BETWEEN DRIVE ELEMENTS (PITCH)

N: ARRAY PATTERN 1
A: ARRAY PATTERN 2
B: ARRAY PATTERN 3

FIG. 11
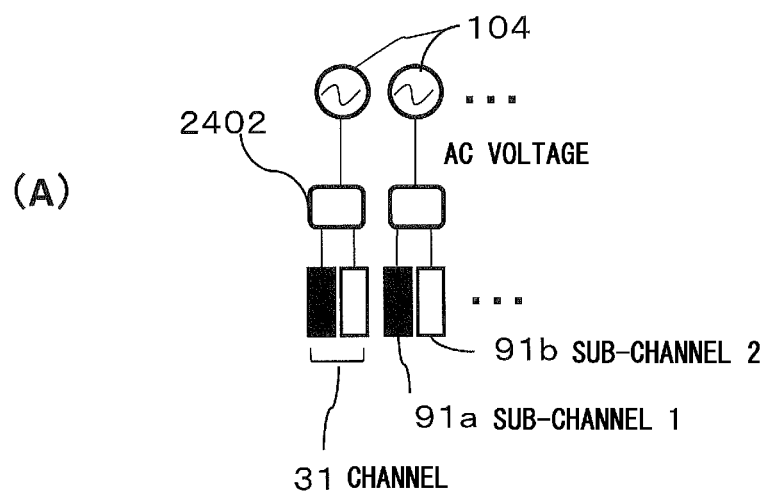
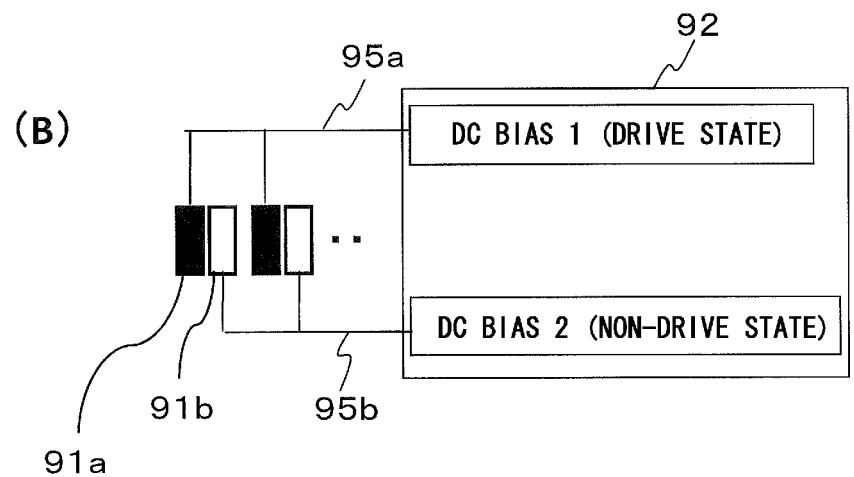

FIG. 16
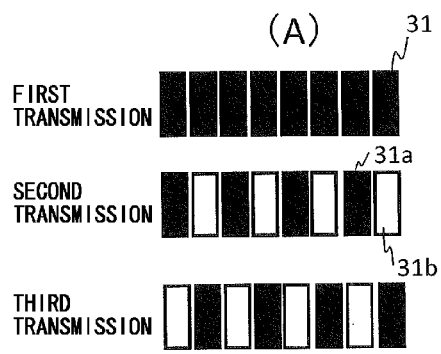
(A)
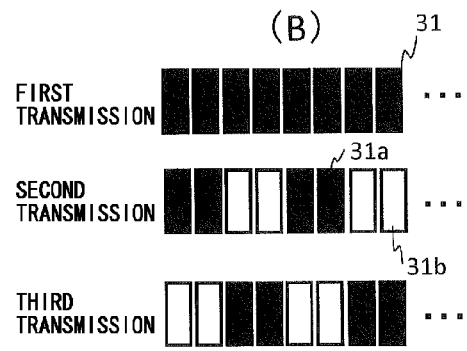
(B)
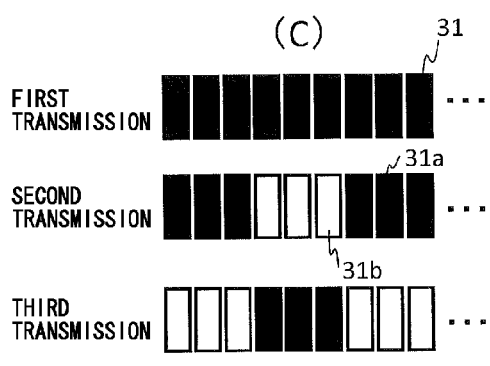
(C)
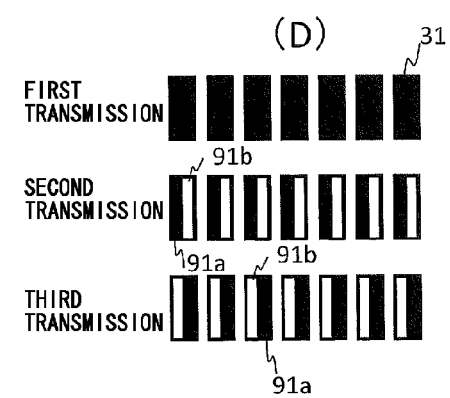
(D)
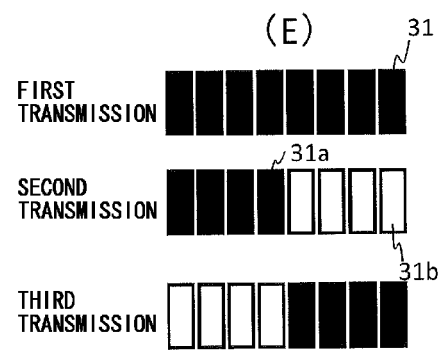
(E)
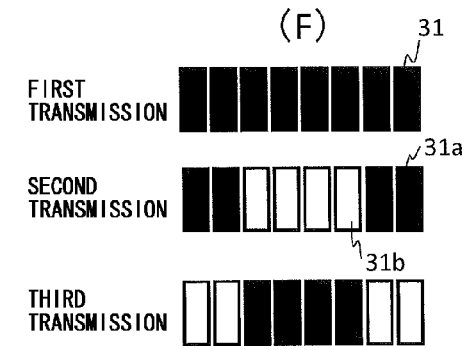
(F)

ULTRASOUND IMAGING APPARATUS

TECHNICAL FIELD

The present invention relates to harmonic imaging in an ultrasound imaging apparatus.

BACKGROUND ART

An imaging technique using an ultrasound wave employs an electroacoustic conversion element (transducer) to convert an electric signal into an ultrasound wave, to irradiate an object with the ultrasound wave, and the electroacoustic conversion element further receives a reflected wave (an echo) which is reflected from the object, so as to convert the reflected wave into an electric signal, thereby displaying on a monitor, image data that is generated based on the electric signal and time-series data. The ultrasound wave passes through the object and a part thereof is reflected on a boundary between different acoustic impedances, and an echo signal having strength depending on a difference of the impedances is generated. Therefore, a display is created assuming the boundary plane as a tomographic image of the object. This kind of imaging technique as described above is widely employed in a nondestructive inspection of a structural object, or as a diagnostic apparatus for performing a minimally invasive imaging to take a tomographic image of a living body.

Along with propagating through the object, the irradiated ultrasound wave may have acoustic waveform distortion. This is because there is a phenomenon caused by acoustic nonlinearity that a part with a high sound pressure in the transmitted acoustic waveform progresses fast, whereas a part with a low sound pressure progresses slowly. Since the longer the acoustic wave propagates, the more this phenomenon is accumulated, and therefore, this intensifies the waveform distortion.

An imaging method for achieving a higher image quality, utilizing this acoustic nonlinearity, is provided in an ultrasonic diagnostic apparatus. When the inner side of a living body is irradiated with the ultrasound wave, waveform distortion is generated in the process of propagation, and a nonlinear component made up of harmonics is generated, in addition to a fundamental frequency component of the irradiated acoustic wave. This nonlinear component is generated in proportion to approximately the square of the amplitude of fundamental wave sound pressure. Therefore, it is possible to create an image with a higher contrast, compared to a normal imaging method according to the fundamental wave, and an image with a high resolution may be obtained. This type of imaging for taking an image of the nonlinear component in a living body tissue is referred to as THI (Tissue harmonic imaging).

In the imaging method according to the THI, the reflection echo strength being generated by the nonlinear component is smaller than the echo strength of the fundamental wave component. Therefore, in order to perform imaging by using only the nonlinear component, it is necessary to separate the nonlinear component from the fundamental wave component to extract the nonlinear component. Conventionally, as a method for extracting the nonlinear component, there are known a method that uses a filter to separate the nonlinear component (e.g., Patent Document 1), PI (Pulse inversion) method (e.g., Patent Document 2), and an amplitude modulation method (e.g., Patent Document 3). Those methods will be explained briefly in the following.

Firstly, a brief explanation will be made as to the method that uses a filter to separate the nonlinear component. When an ultrasound wave with the center frequency $f_0$ is transmitted, the echo signal obtained from the living body contains in a mixed manner, a fundamental wave component (linear component) generated around the center frequency $f_0$ being the same as the transmission frequency, a second higher harmonic component (nonlinear component) generated around the frequency $2f_0$ according to acoustic nonlinearity, and the like. The nonlinear component is generated in a higher frequency region relative to the linear component, and therefore, by filtering the high frequency region, it is possible to extract the nonlinear component.

The PI (Pulse inversion) method transmits two ultrasound pulses, one sound pressure waveform being reversed from the other; positive and negative, to an identical portion of the living body, and adds reflection echoes thereof together. Since the fundamental wave component behaves linearly, when transmission pulses being inversed with each other are transmitted, fundamental wave components of the reflection echoes are also inverted with each other, and they are canceled out by adding together. On the other hand, the nonlinear components (second higher harmonic components) are distorted in a different manner between on the positive side and on the negative side of the sound pressure. Therefore, even though transmission pulses being inverted with each other are transmitted, they do not become waveforms being inverted, and they are not canceled out by adding together. Therefore, if the reflection echoes of the inverted transmission pulses are added together, this may result in that only the nonlinear component remains.

As described in the Patent Document 3, in the amplitude modulation method, transmission of ultrasound wave is performed twice similar to the PI method, but as for the second transmission pulse, sound pressure level (amplitude) is reduced relative to the first transmission pulse, without inverting the sound pressure waveform. By way of example, the amplitude is reduced into half. A nonlinear component (second higher harmonic component) is generated in proportion to the square of the sound pressure of a fundamental wave component. Therefore, the sound pressure of the nonlinear component in the echo signal of the second transmission becomes a quarter relative to the echo signal of the first transmission. Thus, the echo signal of the second transmission is doubled and subtracted from the echo signal of the first transmission, thereby canceling out the fundamental wave components, resulting in remaining of only the nonlinear components.

PRIOR ART DOCUMENT

Patent Document

Patent Document 1
U.S. Pat. No. 5,678,553
Patent Document 2
U.S. Pat. No. 6,095,980
Patent Document 3
U.S. Pat. No. 5,577,505

DISCLOSURE OF THE INVENTION

Problem to be Solved by the Invention

In the aforementioned method for separating the nonlinear component by using a filter, if there is a region (mixed region) where a region of frequency space of the linear component overlaps a region of frequency space of the nonlinear component, a filter band has to be provided on the frequency side sufficiently higher than the mixed region in order to completely extract only the nonlinear component, and therefore it becomes difficult to obtain sufficient signal intensity. Therefore, there is a problem that it is hard to achieve an S/N ratio being required.

In the PI method, in order to cancel out the linear component in the echo signal, it is necessary to form two transmission pulses being completely inverted with each other. Typically, a waveform of a voltage signal that is inputted into an electroacoustic conversion element is inverted, thereby forming a waveform of the transmission pulse. However, if the electroacoustic conversion element responses nonlinearity to a voltage signal, it is not possible to form a completely inverted transmission pulse, even though an inverted input signal is provided. In addition, within a transmission circuit, there are arranged elements for amplifying voltage and those elements have more or less nonlinear response. For the reason above, the nonlinearity in the electroacoustic conversion element and the nonlinearity in the transmission circuit do not allow formation of a completely inverted transmission pulse, failing in completely canceling out the linear component in the echo signal. This makes it difficult to extract the nonlinear component by the PI method.

On the other hand, in the amplitude modulation method, it is necessary to modulate amplitude of the second transmission pulse with respect to the first transmission pulse, for example cutting in half. However, if there exists nonlinearity in the electroacoustic conversion element or in the transmission circuit as described above, there is a problem similar to the PI method that it is not possible to form a transmission pulse in which only the amplitude is reduced to half completely, even though the amplitude of the input signal is reduced to half.

An object of the present invention is to achieve the THI from which more nonlinear components are extracted, even in the case where an electroacoustic conversion element having high nonlinearity is employed.

Means to Solve the Problem

In order to solve the problems above, a first aspect of the present invention provides an ultrasound imaging apparatus as described below. In other words, this ultrasound imaging apparatus includes a transmitter for delivering a transmission signal to multiple electroacoustic conversion elements for driving the electroacoustic conversion elements, and allowing an ultrasound beam to be transmitted to a predetermined position on an imaging target, a receiver for allowing the multiple electroacoustic conversion elements to receive an echo signal of the ultrasound beam from the imaging target to obtain a reception signal, a signal processor for subjecting the reception signal to a computing process and generating an image, and a controller for controlling the transmitter and the signal processor. The controller allows the transmitter to transmit the ultrasound beam twice to an identical position of the imaging target, and allows the signal processor to perform computation such as subtracting on the reception signals being obtained in every transmission performed twice, thereby extracting a nonlinear component included in the reception signals. In one transmission out of transmission performed twice, the transmitter delivers the transmission signal to all the electroacoustic conversion elements that form a predetermined area and drives the electroacoustic conversion elements, out of multiple electroacoustic conversion elements, and in the other transmission, the transmitter delivers the transmission signal selectively only to a part of the electroacoustic conversion elements that form the predetermined area and drives the electroacoustic conversion elements.

Effect of the Invention

According to the present invention, it is possible to establish THI from which nonlinearity has been removed, the nonlinearity being caused by any device including an electroacoustic conversion element and a transmission circuit.

BRIEF DESCRIPTION OF DRAWINGS

FIG. 5(A) and FIG. 5(B) illustrate graphs each showing a sound pressure distribution of the linear component in the ultrasound beam, in the case where the drive channel pattern is changed according to the second embodiment;

FIG. 6 is a table illustrating the drive channel patterns that reduce a grating lobe with respect to each imaging parameter in the second embodiment;

FIG. 11(A) and FIG. 11(B) are block diagrams showing structures for implementing the sub-channels according to the third embodiment;

FIG. 16(A) to FIG. 16(F) each illustrates the drive channel pattern according to the sixth embodiment;

BEST MODE FOR CARRYING OUT THE INVENTION

Figure 1:
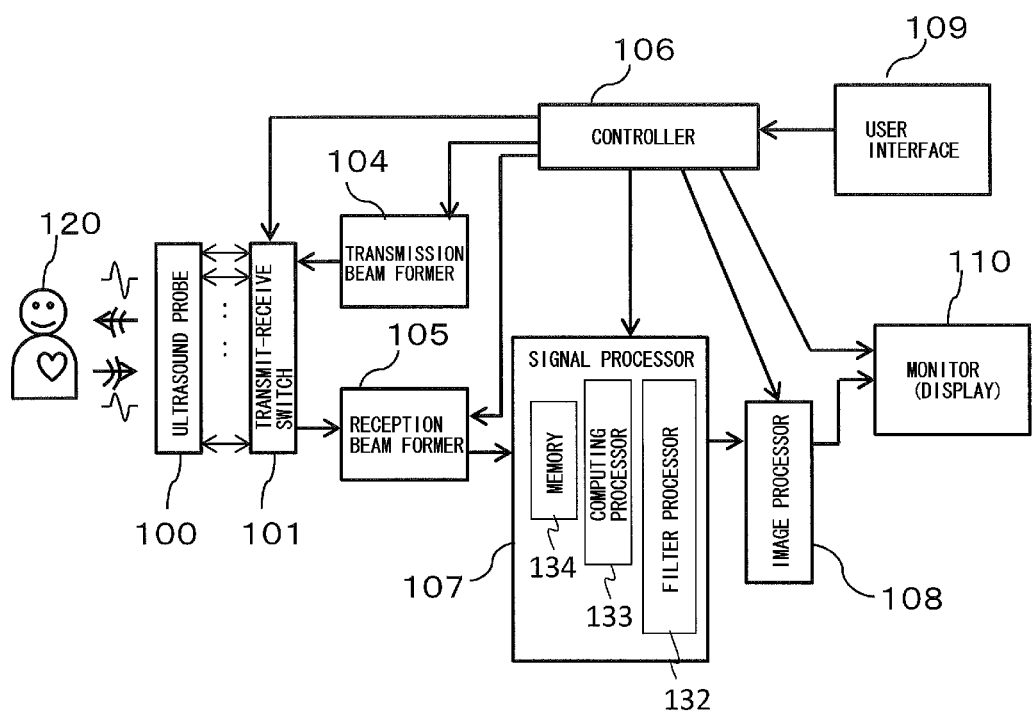
FIG. 1 is a block diagram illustrating an overall configuration of the ultrasound imaging apparatus according to a first embodiment of the present invention.

In the present invention, the ultrasound imaging apparatus as described in the following is provided according to the first embodiment. In other words, the ultrasound imaging apparatus includes a transmitter for delivering a transmission signal to multiple electroacoustic conversion elements for driving the electroacoustic conversion elements, allowing an ultrasound beam to be transmitted to a predetermined position of an imaging target, a receiver for allowing the multiple electroacoustic conversion elements to receive an echo signal of the ultrasound beam from the imaging target to obtain a reception signal, a signal processor for subjecting the reception signal to a computing process to generate an image, and a controller for controlling the transmitter and the signal processor. The controller allows the transmitter to transmit the ultrasound beam twice to an identical position of the imaging target, and allows the signal processor to perform computation such as subtracting, on the reception signals being obtained in every transmission performed twice, thereby extracting a nonlinear component included in the reception signals. In one transmission out of transmission performed twice, the transmitter delivers the transmission signal to all the electroacoustic conversion elements that form a predetermined area and drives the electroacoustic conversion elements, and in the other transmission, the transmitter delivers the transmission signal selectively only to a part of the electroacoustic conversion elements that form the predetermined area and drives the electroacoustic conversion elements.

It is preferable that a waveform of the transmission signal delivered to a part of the electroacoustic conversion elements in the other transmission as described above is the same as the waveform of the transmission signal delivered to the electroacoustic conversion elements in the one transmission.

By way of example, the receiver may be configured in such a manner that an identical electroacoustic conversion element receives each of the echo signals of the ultrasound beams of the transmission performed twice, so as to obtain the reception signals.

The aforementioned multiple electroacoustic conversion elements may be configured in such a manner that they are divided into multiple channels, for instance, and in the other transmission as described above, the electroacoustic conversion elements driven by delivering the transmission signal are selected in units of channel.

It is further possible to configure in such a manner that the aforementioned channel is further divided into multiple sub-channels. For this case, in the other transmission, at least one sub-channel is selected from multiple sub-channels, with respect to each channel, and the transmission signal is delivered to the electroacoustic conversion elements within the sub-channel for driving the electroacoustic conversion elements.

By way of example, it is configured such that the controller described above selects the electroacoustic conversion elements to be driven by the other transmission according to a predetermined pattern depending on imaging parameters, and the transmission signal is delivered thereto. Specifically, the controller is configured to select a pattern in association with the imaging parameters that are accepted by a user interface from an operator.

It is preferable that the controller selects a pattern for minimizing a grating lobe, in association with the imaging parameters. It is further possible to configure such that the controller sets a filtering process in association with the imaging parameters, for extracting the reception signal in a predetermined frequency region, so as to minimize the grating lobe.

The multiple electroacoustic conversion elements as described above may be configured in such a manner as divided into multiple channels, and the channel is further divided into multiple sub-channels. In such a case, in the other transmission as described above, at least one sub-channel is selected from the multiple sub-channels with respect to each channel, and the transmission signal is delivered to the electroacoustic conversion elements within the sub-channel to drive the elements.

The aforementioned channels may be configured to be arranged two-dimensionally, in predetermined long-axis direction and short-axis direction, and it is desirable that the channels being driven in each row along the long axis are arranged at the positions being mutually exclusive between the rows.

It is possible to configure in such a manner that the signal processor performs the filtering process for extracting the reception signal in a predetermined frequency region. The predetermined frequency region is set as a region being equal to or less than $c/d$, when distance between multiple channels being driven is assumed as "d", and a sound velocity within the imaging target is assumed as "c".

The controller may be configured in such a manner that in the other transmission as described above, the controller delivers the transmission signal sequentially to the channels being adjacent to each other.

As the multiple electroacoustic conversion elements, capacitance type electroacoustic conversion elements may be employed. On this occasion, DC bias voltage and an AC voltage signal supplied from the transmitter as the transmission signal are applied to the electroacoustic conversion elements. The controller supplies the DC bias voltage to the electroacoustic conversion elements to which the transmission signal has been delivered selectively by the other transmission, and the controller does not supply the DC bias voltage to the remaining electroacoustic conversion elements, thereby driving the electroacoustic conversion elements being selected.

In the present invention, as the second embodiment, the ultrasound imaging apparatus as described below is provided. That is, the ultrasound imaging apparatus includes a transmitter for delivering a transmission signal to multiple electroacoustic conversion elements arranged on a predetermined ultrasound transmit-receive aperture, for driving the multiple electroacoustic conversion elements, allowing an ultrasound beam to be transmitted to a predetermined position of an imaging target, a receiver for allowing the multiple electroacoustic conversion elements to receive an echo signal of the ultrasound beam from the imaging target to obtain a reception signal, a signal processor for subjecting the reception signal to a computing process and generating an image, and a controller for controlling the transmitter and the signal processor. The controller allows the transmitter to transmit the ultrasound beam different in amplitude at least twice to an identical position of the imaging target, and allows the signal processor to perform computation on the reception signals being obtained in every transmission performed at least twice, thereby extracting a nonlinear component included in the reception signals. The aforementioned transmission performed at least twice includes a transmission for driving all the electroacoustic conversion elements on the ultrasound transmit-receive aperture, and a transmission for driving only the electroacoustic conversion elements within a partial region of the ultrasound transmit-receive aperture.

According to the third embodiment of the present invention, the ultrasound imaging apparatus as described below is provided. That is, the ultrasound imaging apparatus includes a transmitter for delivering a transmission signal to multiple electroacoustic conversion elements for driving the electroacoustic conversion elements, allowing an ultrasound beam to be transmitted to a predetermined position of an imaging target, a receiver for allowing the multiple electroacoustic conversion elements to receive an echo signal of the ultrasound beam from the imaging target to obtain a reception signal, a signal processor for subjecting the reception signal to a computing process and generating an image, and a controller for controlling the transmitter and the signal processor. The controller allows the transmitter to transmit the ultrasound beam at least three times to an identical position of the imaging target, and allows the signal processor to perform computation on the reception signals being obtained in every transmission performed at least three times, thereby extracting a nonlinear component included in the reception signals. In one transmission out of the transmission performed at least three times, the transmitter delivers a transmission signal to all the electroacoustic conversion elements that form a predetermined area and drives the electroacoustic conversion elements, out of the multiple electroacoustic conversion elements, and in at least two remaining transmissions, the transmitter delivers the transmission signal selectively only to a part of the electroacoustic conversion elements that form the predetermined area and drives the electroacoustic conversion elements. The part of the electroacoustic conversion elements being selected in at least two remaining transmissions is selected from the multiple electroacoustic conversion elements forming a predetermined area, in such a manner as being mutually exclusive between the two-time transmissions.

The signal processor subtracts all the reception signals obtained in the remaining transmission performed at least twice, from the reception signal obtained in the first transmission, thereby extracting the nonlinear component included in the reception signal.

It is desirable that according to the remaining transmission performed at least twice, all the multiple electroacoustic conversion elements forming a predetermined area are driven once.

It is possible to configure such that the controller selects the electroacoustic conversion elements to be driven by delivering the transmission signal thereto in every remaining transmission performed at least twice, so that the area formed by those electroacoustic conversion elements becomes constant in each transmission.

Each of the multiple electroacoustic conversion elements may be configured as being divided into multiple channels. On this occasion, in the remaining transmission performed at least twice, the electroacoustic conversion elements to be driven by delivering the transmission signal thereto may be selected in units of channel. By way of example, it may be configured in such a manner that the controller alternately selects a channel to which the transmission signal is delivered for driving the element and a channel to which no transmission signal is delivered, one by one, in the remaining transmission performed at least twice.

The channel as described above may have a structure that it is further divided into multiple sub-channels. In this case, in the remaining transmission performed at least twice, it is possible to select the electroacoustic conversion elements to be driven by delivering the transmission signal thereto, in units of sub-channel. By way of example, in the remaining transmission performed at least twice, it is possible to select alternately one by one, a sub-channel to which the transmission signal is delivered for driving, and a sub-channel to which no transmission signal is delivered, from the multiple sub-channels with respect to each channel.

Hereinafter, an explanation will be made as to the ultrasound imaging apparatus according to one embodiment of the present invention. It is to be noted here that the following explanation will be directed to a medical-use ultrasonic diagnostic apparatus as an example. However, the present invention is not limited to this kind of medical-use apparatus, but it is applicable to any other apparatus for taking an image and creating an image, utilizing ultrasound waves.

First Embodiment

With reference to FIG. 1, an overall structure of the ultrasonic diagnostic apparatus according to the first embodiment will be explained. FIG. 1 is a block diagram illustrating a schematic structure of the ultrasonic diagnostic apparatus. As shown in FIG. 1, this apparatus is provided with an ultrasound probe 100, a transmit-receive switch 101, a transmission beam former 104, a reception beam former 105, a controller 106, a signal processor 107, an image processor 108, a user interface 109, and a monitor 110.

The ultrasound probe 100 includes electroacoustic conversion elements (transducer elements) that converts an electric signal to an acoustic wave, and converts an acoustic wave to an electric signal. Those electroacoustic conversion elements are arranged to constitute an ultrasound transmit-receive aperture as a predetermined array one-dimensionally or two-dimensionally in the probe 100. An outside shape of the probe 100 is formed in such a manner that it is suitable for the use to bring a surface of the ultrasound transmit-receive aperture into contact with the imaging target 102.

Multiple electroacoustic conversion elements being arranged are divided virtually or physically into a predetermined multiple channels. Each channel is made up of at least one electroacoustic conversion element.

Figure 2:
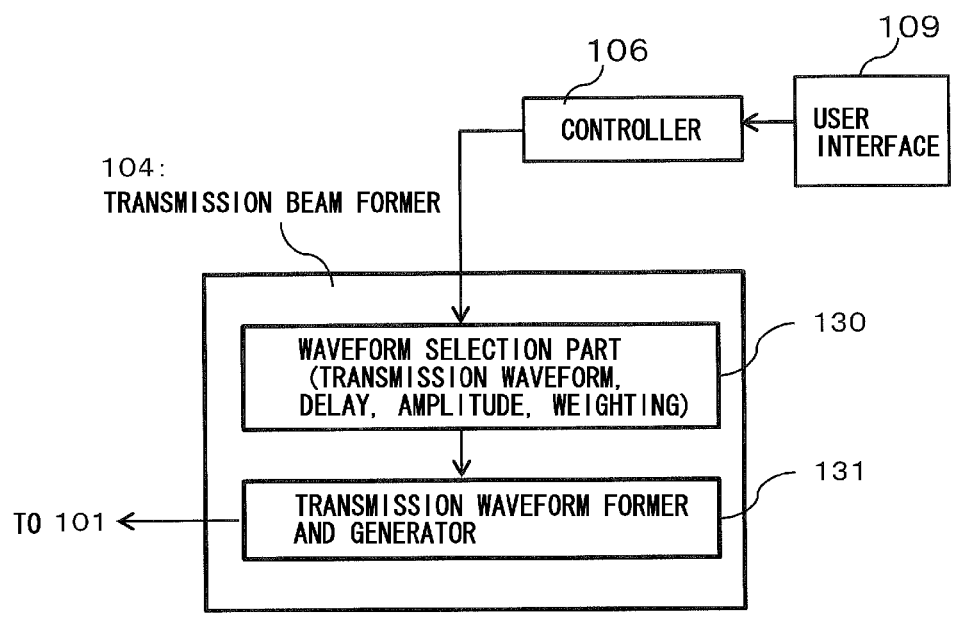
FIG. 2 is a block diagram illustrating a transmission beam former of the apparatus as shown in FIG. 1.

As shown in FIG. 2, the transmission beam former 104 includes a waveform selection part 130, and a transmission waveform former and generator 131. The waveform selection part 130 selects a waveform type, a delay time setting, amplitude modulation, weighting, and the like, for each channel from a predetermined range. They are associated with parameter values (transmission frequency, waveform number, transmission wave focusing position, amplitude, and the like) which the user interface 109 accepts from a user. The transmission waveform former and generator 131 generates a transmission waveform (a transmission signal) using the values selected by the waveform selection part 130 for each channel, and delivers the transmission signal to the transmit-receive switch 101.

Accordingly, under the control of the controller 106, the transmission beam former 104 outputs a transmission electric signal having a delay time being adjusted to the transmission focal point with respect to each channel, and the transmission electric signal is delivered to the electroacoustic conversion elements constituting each channel of the ultrasound probe 100, via the transmit-receive switch 101.

Each of the electroacoustic conversion elements converts the transmission electric signal to an acoustic wave. Each of the electroacoustic conversion elements issues the acoustic wave (transmission pulse), thereby forming an acoustic field (an ultrasound beam or a transmission beam) focusing on a point at the focal position set by a user.

Each of the electroacoustic conversion elements of the probe 100 receives an echo signal of the ultrasound beam (transmission beam) reflected from the imaging target 120, and the echo signal is converted into an electric signal (reception signal). The reception signals of the respective electroacoustic conversion elements are delivered to the reception beam former 105 via the transmit-receive switch 101. The reception beam former 105 provides a delay to the received echo signals, and forms a reception beam. Signals obtained from the reception beam are delivered to the signal processor 107. The signal processor 107 includes a filter processor 132, a computing processor 133, and a memory 134. The signal processor 107 performs an amplifying process, a predetermined filtering process, and a signal computing process on the signals obtained from the reception beam, under the control of the controller 106. The amplifying process is performed according to TGC (time gain compensation), an amplification factor, and the like, being set by the user via the user interface 109. If necessary, the memory 134 stores the signals temporarily. The output from the signal processor 107 is delivered to the image processor 108, and then image data and time-series data are structured. The image data and the time-series data are outputted to the monitor 110 and displayed thereon.

The controller 106 controls a series of operations in each part of those described above. The controller 106 implements an imaging method according to the THI (Tissue harmonic imaging). The user interface 109 accepts from the user, an instruction for operating the overall apparatus, a selection of the imaging method, parameters necessary for the imaging, and the like.

A configuration of the ultrasonic diagnostic apparatus shown in FIG. 1 excepting the ultrasound probe 100, may be mounted on an enclosure as a main unit being separated from the ultrasound probe 100, or a part of the configuration may be included in the probe 100.

An explanation will be made as to the imaging method according to the THI that is implemented by the ultrasonic diagnostic apparatus of the present embodiment.

Figure 18:
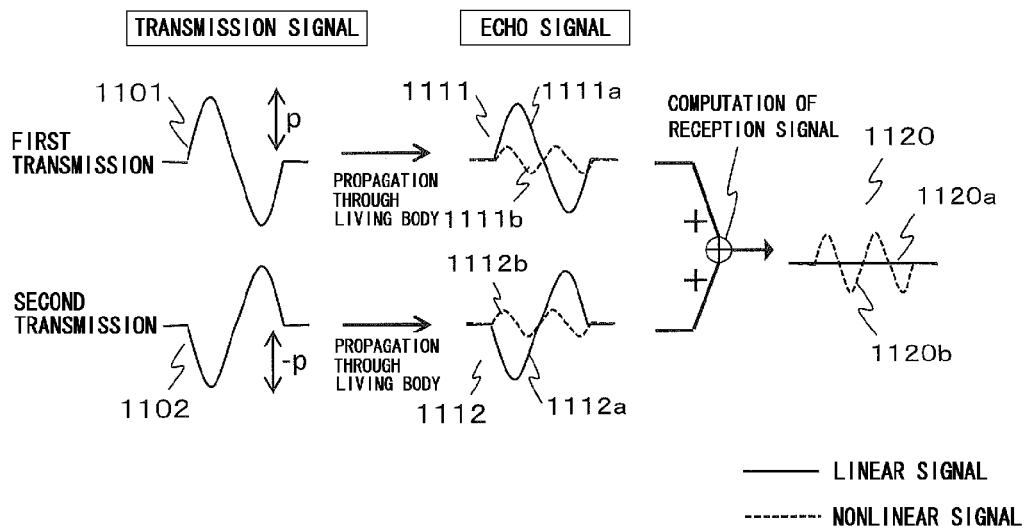
FIG. 18 illustrates the PI method that is used as a conventional THI method.

The PI method and the amplitude modulation method conventionally used as the THI, perform transmissions twice, and perform computing on the echo signals obtained by the respective transmissions, thereby extracting a nonlinear signal. FIG. 18 illustrates the PI method. The echo signal 1111 obtained by the first transmission using the transmission signal 1101 is received, which consists of a linear component 1111a with a nonlinear component 1111b generated during wave propagation in a living body. A waveform of the transmission signal 1102 in the second transmission is inverted in phase by 180 degrees with respect to the waveform of the transmission signal 1101 in the first transmission, and the linear component 1112a included in the obtained echo signal 1112 also takes the form being inverted with respect to the component 1111a. On the other hand, the phase of the nonlinear component 1112b included in the echo signal 1112 in the second transmission is not inverted. Therefore, when computing the sum of the first and the second echo signals is performed, the linear component 1120a in a echo signal after the computation 1120 becomes zero. Accordingly, only the nonlinear component 1120b remains.

Figure 19:
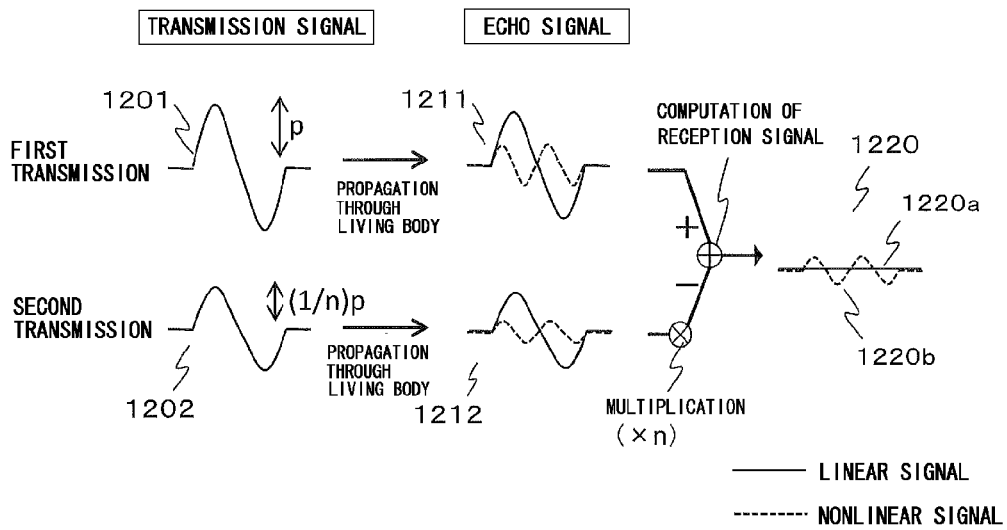
FIG. 19 illustrates the amplitude modulation method that is used as a conventional THI.

As shown in FIG. 19, in the amplitude modulation method, a waveform amplitude of the transmission signal 1202 in the second transmission is modulated, so as to be 1/n (n>1) relative to the waveform amplitude of the transmission signal 1201 in the first transmission. The echo signal 1212 obtained by the second transmission includes a linear component with 1/n sound pressure and a nonlinear component with $1/n^2$ sound pressure, with respect to them in the echo signal 1211 for the first transmission. Therefore, by performing computation such as multiplying the echo signal 1212 in the second transmission by n, and subtracting the multiplied signal from the echo signal 1211 in the first transmission, the linear component 1220a of a echo signal after the computation 1220 becomes zero. Accordingly, only the nonlinear component 1220b remains.

In the PI method, it is necessary to invert the phase of the second transmission pulse by 180 degrees completely with respect to the first transmission pulse. In the amplitude modulation method, the amplitude of the second transmission pulse has to be modulated precisely. In other words, it is necessary to make the waveform precisely for the second transmission pulse. However, if the nonlinearity of the electroacoustic conversion element and/or the nonlinearity of the transmission circuit is large, it is not possible to make the transmission waveform precisely even though the signal electric waveform which is inverted or amplitude modulated precisely input into the electroacoustic conversion element. Thereby, it becomes difficult to completely cancel out the linear components in the echo signals obtained by performing computation on the two echo signals. This results in that a signal influenced by the nonlinearity of the electroacoustic conversion element or the circuit is mixed into the echo signals, and it means not to extract only the nonlinear component being generated by the living body propagation in the imaging target 120.

In the present embodiment, to execute the amplitude modulation method, the sound pressure (amplitude of sound wave) of the overall transmission beam is adjusted by changing a drive area (corresponding to the number of the electroacoustic conversion elements being driven) on the ultrasound transmit-receive aperture of the ultrasound probe 100. In other words, upon transmitting the second transmission beam, the drive area on the ultrasound transmit-receive aperture is made smaller relative to that for the first transmission beam, thereby reducing the sound pressure of the second transmission beam. This is because the transmitted sound pressure is proportional to the drive area within the ultrasound transmit-receive aperture. On this occasion, the waveform of the transmission electric signal inputted into the electroacoustic conversion elements that are driven in the first transmission is identical to the waveform of the transmission signal inputted into the electroacoustic conversion elements that are driven in the second transmission. With this configuration, the waveform of the transmission electric signal being supplied is identical between the first and second transmission beams when they are sent out. Therefore, it is possible to transmit a pulse that is not influenced by the nonlinearity of the electroacoustic conversion element and/or the circuit, as well as reducing the sound pressure of the transmission beam.

In the present embodiment, upon the second transmission, each channel within the ultrasound transmit-receive aperture may be selected to be a channel to be driven (drive channel) and a channel not to be driven (non-drive channel). Upon the second transmission, the transmission electric signal having the same waveform as that of the first transmission signal is inputted in the electroacoustic conversion elements of the drive channel. The transmission electric signal is not inputted in the non-drive channel upon the second transmission (the signal voltage is set to be zero). With this configuration, it is possible to obtain a transmission beam with a desired sound pressure by selecting a proper ratio of the drive channels to the non-drive channels.

Upon transmission, the overall region of the ultrasound transmit-receive aperture for the case where a region of driven channels becomes the largest is referred to as "aperture upon transmission", and its long diameter is referred to as "transmission bore". FIG. 3(A) to FIG. 3(E) illustrates examples of the channel arrangement within the aperture upon transmission and selection examples of the drive channels upon the second transmission. In the apertures upon transmission as illustrated in FIG. 3(A) to FIG. 3(E), the channels 31 made up of 12 channels are arranged in a line in the direction of the transmission bore (long diameter). The number of channels in the short diameter direction of the aperture upon transmission is one. Each channel 31 is made up of multiple electroacoustic conversion elements being arranged. It is to be noted that in FIG. 3(A) to FIG. 3(E), to facilitate understanding, there is provided a gap between adjacent channels 31, but in the actual ultrasound probe 100, no gap may be provided between those adjacent channels 31 in some cases.

Figure 3:
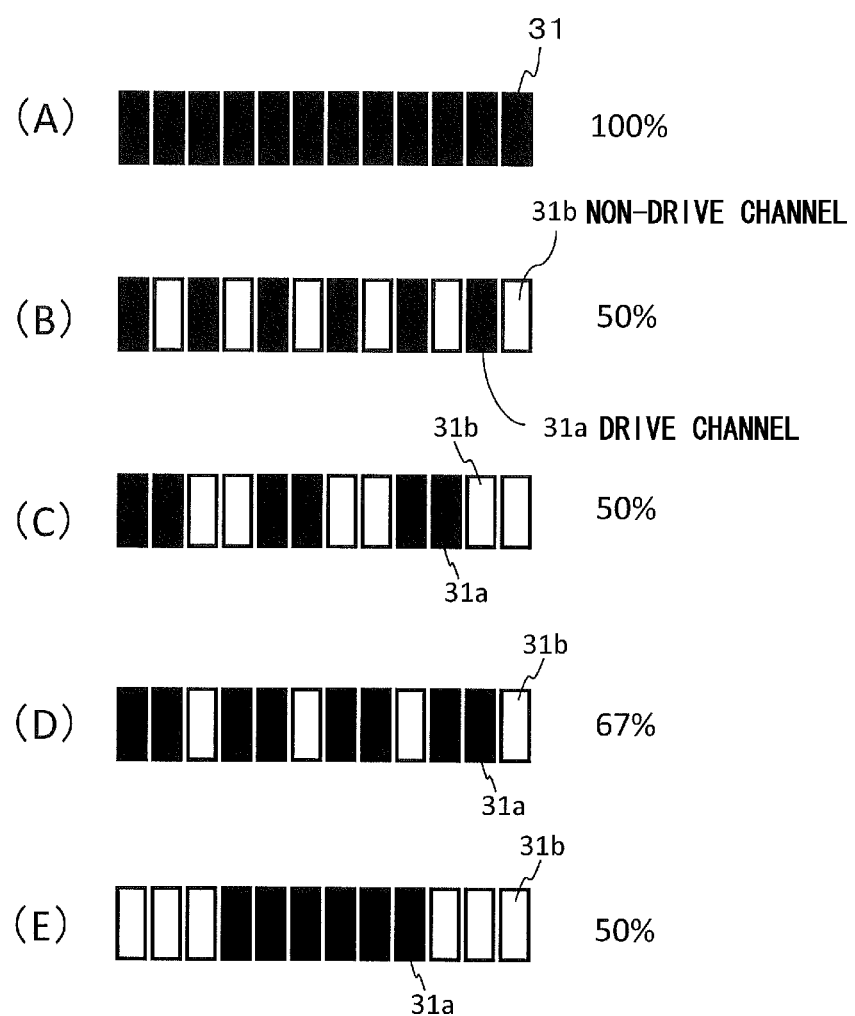
FIG. 3(A) to FIG. 3(E) each illustrates an example of a drive channel pattern upon performing the imaging of the first embodiment.

FIG. 3(A) illustrates drive channels upon transmitting the first transmission beam, and all the channels 31 are driven within the aperture upon transmission. FIG. 3(B) to FIG. 3(E) illustrate the drive channels upon transmitting the second transmission beam, and each of FIGS. 3(B), (C), and (E) illustrates a selection example in which a half of the drive channels is set as drive channels upon the first transmission. In FIG. 3(B), the drive channel 31a and the non-drive channel 31b are arranged alternately one by one, in FIG. 3(C), the drive channel 31a and the non-drive channel 31b are arranged alternately two by two, and in FIG. 3(E), the drive channels 31a are continuously arranged around the center of the aperture upon transmission, and non-drive channels 31b are placed on both sides. As illustrated in FIG. 3(B), FIG. 3(C), and FIG. 3(E), even though the way of selection or arrangement of the drive channels 31a is different, the sound pressure of the second transmission beam is rendered to be half of that of the first transmission, as far as the drive area is half of the entire aperture upon transmission. FIG. 3(D) shows an example that two-thirds of the drive channels upon the first transmission are set as being driven, and one non-drive channel is arranged every three channels.

Figure 4:
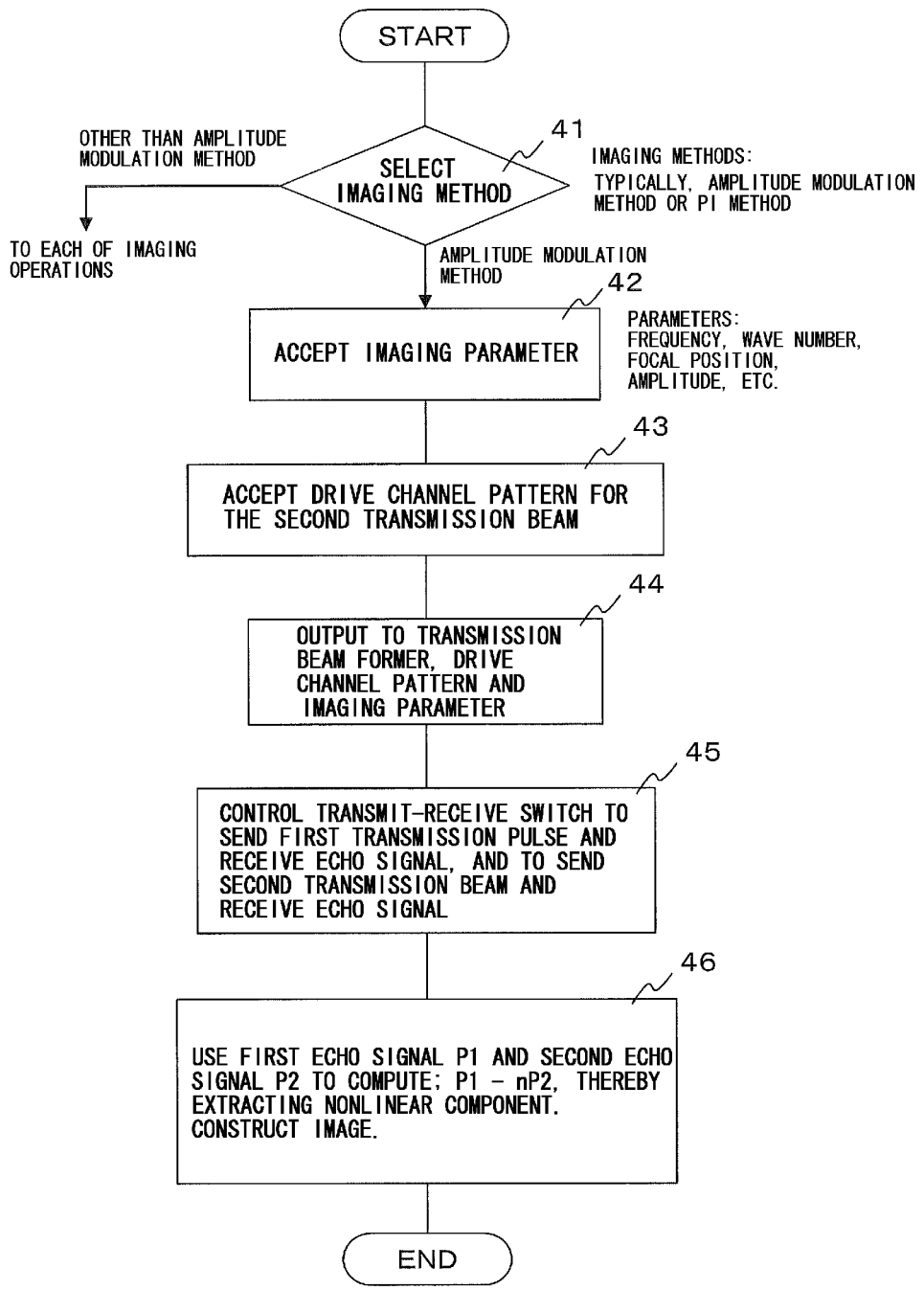
FIG. 4 is a flowchart illustrating a flow of the imaging operation of the first embodiment.

Hereinafter, with reference to the flowchart of FIG. 4, operations of each part will be explained, in the case where imaging is performed according to the amplitude modulation method of the present embodiment. The controller 106 reads out and executes the programs being stored in advance in a built-in memory, thereby controlling each part as illustrated in the flowchart of FIG. 4 and executing the imaging.

Firstly, in the step 41, the controller 106 displays a screen prompting the user to select an imaging method on the monitor 110, and when the user selects the imaging method via the user interface 109, the controller accepts the selection (step 41). By way of example, it is displayed that any imaging method is selectable from the options, which are including the amplitude modulation method of the present embodiment, the PI method, a normal imaging method other than the THI, and the like.

In the step 41, if the imaging method selected by the user is the amplitude modulation method, the controller 106 proceeds with processing to the step 42, displays a screen for accepting an imaging parameter on the monitor 110, and accepts from the user an input of the imaging parameter via the user interface 109. The imaging parameter being accepted may include frequency, a wave number, a focal position, amplitude of a transmission pulse, TGC, gain, and the like, upon processing a reception signal. As for the amplitude of the transmission beam, it is also accepted that both the amplitudes of the first transmission and second transmission. The amplitude of the second transmission is set to be multiplied by 1/n (n>1). It is to be noted that the user may not necessarily select all of those imaging parameters, but the controller 106 may be allowed to select prepared parameters according to the imaging method.

In the step 41, if the user selects an imaging method other than the amplitude modulation method, the process moves on to the step for executing thus selected imaging method (not illustrated).

When the imaging parameters are accepted in the step 42, the process moves on to the step 43, and there are displayed on the monitor 110 selectable drive channel patterns of the ultrasound probe 100 upon transmitting the second transmission beam, and selection by the user is accepted via the user interface 109. Specifically, in the built-in memory, multiple types of drive channel patterns as shown in FIG. 3(B) to FIG. 3(E) are stored in advance, and at least one drive channel pattern is displayed on the monitor 110, the pattern being associated with the magnitude of the amplitude of the second transmission beam as accepted from the user in the step 42. By way of example, if the user inputs in the step 42 that the amplitude of the second transmission beam is set to be ½ (50%) of the amplitude of the first transmission beam, the controller 106 displays the patterns as shown in FIG. 3(B), FIG. 3(C), and FIG. 3(E) on the monitor 110. If the user inputs that the amplitude of the second transmission beam is set to be ⅔ (approximately 67%) of the amplitude of the first transmission beam, the controller 106 displays the patterns as shown in FIG. 3(D) on the monitor 110. If the user selects a pattern from the multiple drive channel patterns being displayed, the process moves on to the step 44.

Instead of selecting from the multiple patterns by the user in the step 43, the controller 106 is allowed to select the prepared pattern which may be prepared according to the amplitude of the second transmission beam.

In the step 44, the controller 106 delivers to the transmission beam former 104, the imaging parameters accepted in the step 42 (transmission frequency, wave number, transmission focal position, amplitude, and the like), and the drive channel pattern of the second transmission beam being selected in the step 43. The transmission beam former 104 generates a transmission signal for the first transmission beam. In other words, the waveform selection part 130 selects from a predetermined range, a waveform type, delay time for each channel, amplitude, weighting, and the like, in association with the imaging parameters. Subsequently, the transmission waveform former and generator 131 generates a transmission waveform (transmission signal) with respect to each channel, using the values selected by the waveform selection part 130.

In the step 45, the controller 106 performs switching operation on the transmit-receive switch 101, and delivers the first transmission signal to the electroacoustic conversion elements that constitute each of the channels in the aperture upon transmission of the ultrasound probe 100. As shown in FIG. 3(A), the transmission signal for the first transmission beam is delivered to the electroacoustic conversion elements of all the channels 31 within the aperture upon transmission of the ultrasound probe 100. Accordingly, an ultrasound beam (transmission beam) having predetermined amplitude is transmitted to the imaging target 120.

Upon receiving, the electroacoustic conversion elements within the aperture of the ultrasound probe 100 receive an echo signal from the living body of the imaging target 120, and the reception signal is converted into an electric signal. The controller 106 performs switching operation on the transmit-receive switch 101, and delivers the reception signal to the reception beam former 105. The reception beam former 105 provides delay to the echo signal being received, forms a reception beam signal, and delivers the signal to the signal processor 107. The signal processor 107 temporarily stores the reception beam signal in the memory. It is to be noted here that the aperture upon receiving does not necessarily coincide with the aperture upon transmission.

Next, the transmission beam former 104 generates a transmission signal for the second transmission beam. The waveform of the second transmission signal is set to be identical to the waveform of the first transmission signal for the drive channel 31a of the drive channel pattern selected in the step 44. As for the non-drive channel 31b, no transmission signal is generated, or a signal with zero voltage is generated. The controller 106 performs switching operation on the transmit-receive switch 101, and delivers the transmission signal from the transmission beam former 104 to the ultrasound probe 100.

Accordingly, the ultrasound probe 100 issues a wave of the second transmission beam from only the drive channel 31a. The sound pressure of the second transmission beam is smaller than that of the first transmission beam. The second transmission beam has a waveform not influenced by nonlinear responsivity of the electroacoustic conversion element, and has a waveform as to which only the amplitude is modulated with respect to the first transmission beam.

Similar to the case of the first transmission beam, the electroacoustic conversion elements within the aperture upon receiving of the ultrasound probe 100 receive the echo signal of the second transmission beam from the living body. The controller 106 performs switching operation on the transmit-receive switch 101, delivers the reception signal to the reception beam former 105, and further delivers the reception beam signal to the signal processor 107. It is desirable that the aperture upon receiving for the first time should coincide with the aperture upon receiving for the second time. Under the actual use conditions, the aperture upon receiving may be weighted in some cases, and the signals received by the electroacoustic conversion elements on both edges of the aperture upon receiving may become sufficiently smaller than the signals received by the electroacoustic conversion element around the center. In that case, it is allowable that the aperture upon receiving for the first time is different from the aperture upon receiving for the second time. This is because, for creating an image, the influence caused by the difference between those apertures upon receiving is small, and the same result may be obtained just like the case where the apertures are made identical.

In the step 46, the controller 106 performs a computing process on the first and the second echo signals, and allows the signal processor 107 to extract only the nonlinear component. The signal processor 107 applies an amplifying process and a predetermined filtering process to the reception signal obtained from the reception beam signal, then multiplying the reception signal of the second echo signal by n, and subtracting the result from the reception signal of the first echo signal.

This process will be explained specifically. When the sound pressure of the first transmission beam is assumed as p, the sound pressure level of the linear component is represented by P that is proportional to p. Since the sound pressure level of the nonlinear component (the second harmonic) is proportional to $P^2$, the sound pressure of the entire echo signals can be expressed by $P+\alpha P^2$ ($\alpha$ is an arbitrary number). As shown in FIG. 3(D), if the drive channels 31a upon transmission of the second transmission beam occupies ⅔ in size of the drive area in the aperture upon transmission, the sound pressure of the second transmission beam is equal to (⅔)p, and the sound pressure of the echo signals is expressed by $(⅔)P+\alpha(4/9)P^2$. In order to extract only the nonlinear component from those two echo signals, it is only required to multiply the second echo signal by 3/2, and subtract the result from the first echo signal. According to this computation, the term P is canceled out, and only $\alpha(⅓)P^2$ remains, thereby achieving extraction of the nonlinear component only. Similarly, it is also possible to extract only the nonlinear component by multiplying the first echo signal ⅔, and subtracting the second echo signal therefrom.

Therefore, assuming that the amplitude of the second transmission beam set by the user in the step 42 is 1/n (n>1) of the amplitude of the first transmission beam, the signal processor 107 performs computation as $P_1-nP_2$ or $(1/n)P_1-P_2$, where $P_1$ and $P_2$ are the echo signals for the first and the second transmission beams, respectively. Accordingly, the linear components are canceled out, and it is possible to leave only a component which is associated with the nonlinear component $(1-(1/n))P^2$ or $(1/n)(1-(1/n))P^2$.

The obtained nonlinear component is thus delivered to the image processor 108, thereby constructing image data. Consequently, an image according to the THI is obtained.

It is desirable that the value of 1/n is set to be as small as possible, and as the computation process, $P_1-nP_2$ is carried out. This is because this may allow extraction of a larger amount of the nonlinear component. In other words, the number of channels to be driven (drive area) within the aperture upon transmission of the ultrasound probe 100 is made as small as possible in the second transmission, thereby increasing the nonlinear component obtained after the computing process on the reception signals.

In the explanation above, the first transmission beam setting all the channels in the aperture upon transmission as drive channels 31, after that, the second transmission beam is transmitted with setting only a part of the channels as the drive channels 31a. However, it is possible to change the order of transmissions, between the first transmission and the second transmission. And, it is possible to use any channels within the ultrasound transmit-receive aperture arranged of the probe as the aperture upon transmission.

As thus described, the present embodiment is directed to the ultrasound imaging apparatus including the transmission beam former 104 for delivering the transmission signal to the multiple electroacoustic conversion elements for driving the elements being arranged in the ultrasound probe 100 as illustrated in FIG. 1, and transmitting an ultrasound beam to a predetermined position of the imaging target 120, the reception beam former 105 for allowing the multiple electroacoustic conversion elements to receive an echo signal of the ultrasound beam from the imaging target 120 to obtain a reception signal, the signal processor 107 for performing the computing process on the reception signal and generating an image, and the controller 106 for controlling the transmission beam former 104 and the signal processor. The controller 106 allows the transmission beam former 104 to transmit the ultrasound beam twice, directed to an identical position on the imaging target 120, allows the signal processor 107 to perform the computing process on the reception signals respectively obtained in the transmission performed twice, thereby canceling out the linear component included in the reception signals, and extracting the nonlinear component. In one transmission out of the transmission performed twice, the transmitter delivers the transmission signal to drive all the electroacoustic conversion elements corresponding to a predetermined area (aperture upon transmission) among the multiple electroacoustic conversion elements, and in the other transmission, the transmission signal is selectively delivered to drive only a part of the electroacoustic conversion elements corresponding to the predetermined area. In other words, the amplitude of the transmission beam is modulated by reducing the number of drive channels (drive area), and therefore input voltage applied to the electroacoustic conversion elements of driven channels in both transmission performed twice has a completely identical waveform. Consequently, there is no influence of waveform distortion due to voltage dependence caused by nonlinearity of the device such as the electroacoustic conversion element, and it is possible to extract only the nonlinear component with a high degree of precision, the nonlinear component being generated by propagation through the living body.

Second Embodiment

The ultrasonic diagnostic apparatus according to the second embodiment will be explained.

Similar to the first embodiment, the ultrasonic diagnostic apparatus of the second embodiment transmits a transmission beam twice, and in one transmission, the number of drive channels (drive area in the aperture upon transmission) is made less (smaller) than that of the other transmission, thereby modulating the amplitude of the transmission beam, and performing the THI according to the amplitude modulation method. In the second embodiment, further considering a grating lobe being generated, an appropriate drive channel pattern is made selectable for reducing the linear component being left uncanceled, so as to suppress an artifact (a virtual image in the image).

Firstly, the grating lobe will be explained. Generally, in an ultrasound probe being a type of electronically scanned array, wave fronts of the ultrasound waves emitted respectively from the electroacoustic conversion elements in an array are combined to generate a transmission beam. Each of the electroacoustic conversion elements is provided with a delay with respect to each channel, so that the phase of the ultrasound wave coincides with an aimed direction (main axis). Since a transmission pulse emitted from the electroacoustic conversion element includes multiple waves, another wave front may be formed in combination with a delayed phase of pulse emitted from the electroacoustic conversion element in the adjacent channel. Therefore, a beam is generated also in the direction different from main axis by that wave front. Accordingly, upon receiving, an intensive echo signal from the direction different from the main axis. This beam having directivity different from the main axis is referred to as a grating lobe.

If it is assumed that a distance between adjacent channels (pitch) is referred to as "d", and a wavelength of the ultrasound wave is assumed as $\lambda$, the grating lobe appears in the direction from the main axis by $\theta=\sin^{-1}(m\lambda/d)$ (here, m is an integer). In other words, if the pitch d and the wavelength $\lambda$ are configured in such a way that $\theta$ is positioned outside of the field of view, generation of the grating lobe may be prevented. The grating lobe is less likely to be generated, as the pitch d is set to be smaller in case for the frequency of the pulse is fixed.

In the first embodiment, in one transmission out of the transmission performed twice, the number of drive channels (drive area in the aperture upon transmission) of the ultrasound probe 100 is set to be smaller than the total number of channels (the entire region of the aperture upon transmission), and as a result, the THI in which the device nonlinearity is eliminated is performed. In a typical ultrasound probe 100, the pitch d of the channel is designed in such a manner that any grating lobe may not be generated with respect to the frequency of a transmission pulse. If a drive channel pattern is selected for reducing the drive area in the transmission aperture, this selected pattern may create a situation that the pitch d is enlarged, and in some cases, this may result in that a condition for originating the grating lobe is satisfied.

Hereinafter, this situation will be explained specifically. FIG. 5 shows a linear-component acoustic field of the transmission beam in proximity to a focus depth of 20 mm obtained by simulation where a linear-array probe was used as the ultrasound probe 100. In the simulation, it was assumed that the sound velocity in the living body was 1,500 m/s, and the attenuation coefficient was 0.5 dB/cm/MHz. It was also assumed that the channel pitch d was 0.2 mm, being made up of 42 channels in total, and the transmission bore was approximately 8.4 mm. The vertical axis of the graph in FIG. 5(A) represents the sound pressure, and the horizontal axis represents the angle in the azimuth direction indicated by sine function, and the main axis of the transmission beam was in the direction of $\sin \theta=0$.

All plots as shown in FIG. 5(A) represents a sound pressure distribution in the case where a transmission pulse has center frequency 9 MHz and fractional bandwidth 70%. The plot 1901 represents a case of all the channels were driven. Here, the fractional bandwidth is obtained by dividing a band in the transmission spectrum by the center frequency.

The plot 1902 indicates a sound pressure distribution of the transmission beam in the case where the drive area was made half relative to the case where all the channels were driven, by using the drive channel pattern in which the drive channel 31a and the non-drive channel 31b were set alternately as shown in FIG. 3(B). It is to be noted that both the plot 1901 and the plot 1902 were normalized at their maximum sound pressure, respectively.

Comparing the plot 1901 with the plot 1902, a good coincidence in proximity to the main axis (in the direction of $\sin \theta=0$) can be seen, but as for the plot 1902, a rise of sound pressure in proximity to the azimuth angle over $\sin \theta=0.5$ appears, and thus there is a large difference in the acoustic field between those plots. This is because in the case of the plot 1902, the drive channels 31a were arranged alternately, relative to the actually arranged channels, and therefore, the channel pitch was substantially twice as large as the actual channel pitch d, failing to completely suppress generation of the grating lobe. When the grating lobe occurs, the linear component caused by the grating lobe cannot be canceled out by the computing process of the step 46 as shown in FIG. 4, even though the linear component on the main axis is canceled out to extract a nonlinear component in an echo signal. Therefore, the linear component remains in the signal after the process. In other words, the signal generated by the linear component residual after canceling out is displayed on the image, simultaneously with the nonlinear component, and this may cause an artifact (a virtual image in the image). Therefore, it is desirable to suppress the grating lobe as possible. As described above, when the distance between the adjacent drive channels 31a becomes larger than the width of one channel as shown in FIG. 3(B), the grating lobe occurs. Thus, it is necessary to set the distance between the drive channels 31a according to an allowable range for suppressing the grating lobe. By way of example, it is preferable that the distance is less than the two channels' width.

The plot 1903 in FIG. 5(A) indicates a sound pressure distribution of the transmission beam in the case where the drive channel pattern was formed as shown in FIG. 3(E), and the other conditions were set in the same manner as those of the plot 1902. In the drive channel pattern as shown in FIG. 3(E), the drive channels 31a were arranged collectively around the center in the aperture upon transmission, the pitch d between the adjacent drive channels was not enlarged even though the drive area was reduced, and therefore, the grating lobe did not occur in the plot 1903. Therefore, the plot 1903 became close to the acoustic field of the plot 1901. In this situation, when the linear component on the main axis is canceled out by the computing process in the step 46 of FIG. 4 and the nonlinear signal is extracted, the linear component in the echo signal being residual after the processing becomes smaller than the case of the plot 1902.

As thus described, it is found that by selecting an appropriate pattern as the drive channel pattern, it is possible to suppress generation of the grating lobe, reducing the linear signal which remains without being canceled out.

In the second embodiment, drive channel patterns which allow suppression of the grating lobe are stored in the memory in advance within the controller 106, forming a table, or the like, as shown in FIG. 6. Those drive channel patterns are obtained by computation or experiment in advance, according to the channel pitch d of the ultrasound probe 100 being mounted and the imaging parameters set by the user, such as the frequency, wave number, focal depth of the transmission pulse.

Figure 7:
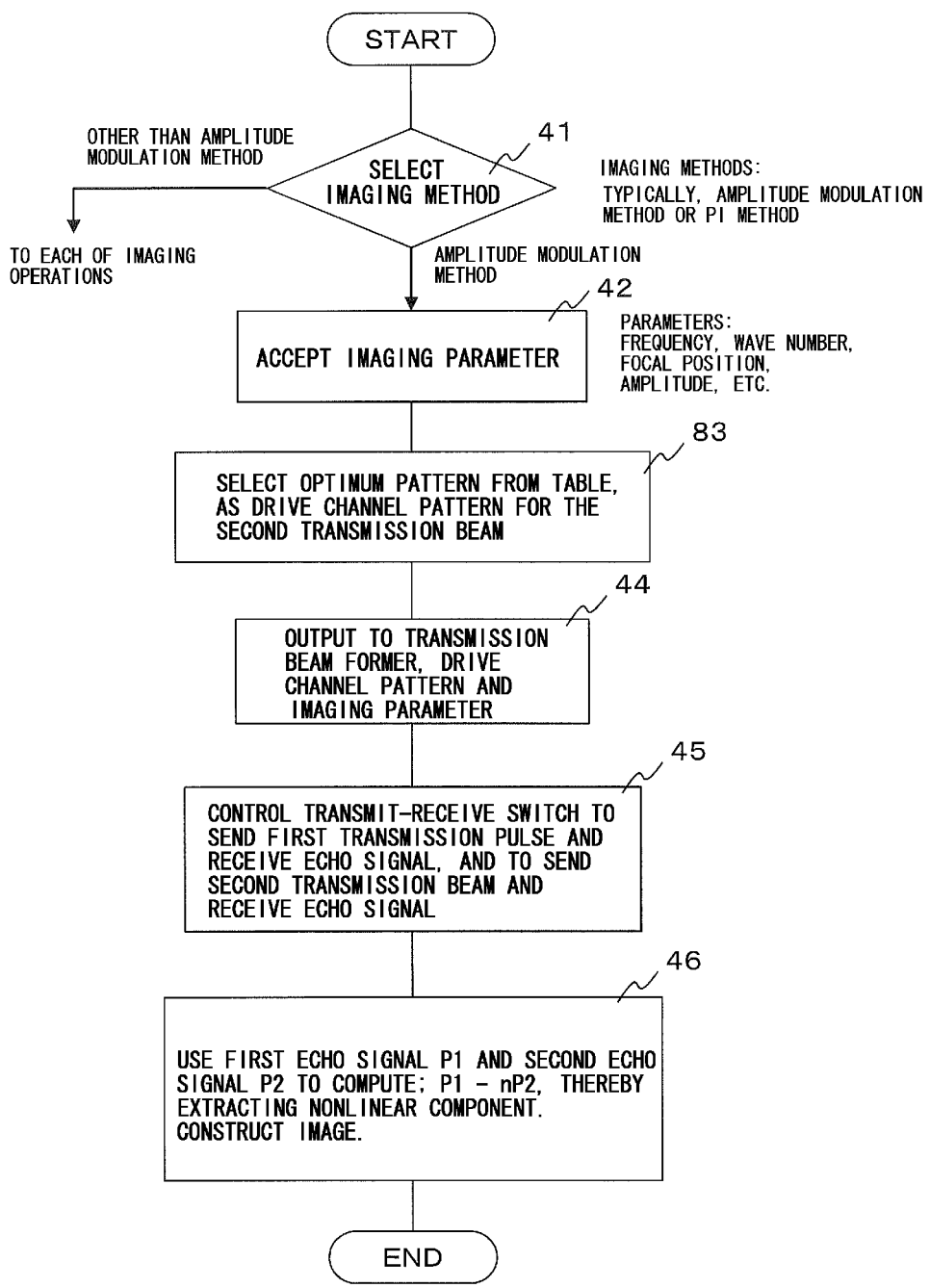
FIG. 7 is a flowchart illustrating a flow of the imaging operation according to the second embodiment.

As shown in the flow of FIG. 7, in the imaging method according to the second embodiment, if inputting of the imaging parameter such as the frequency, wave number, and focal position, and amplitude, is accepted from the user in the step 42, the process moves on to the step 83, and the controller 106 reads an optimum drive channel pattern from the table as shown in FIG. 6 in the memory, in association with the frequency, wave number, and focus depth set as the imaging parameter. By way of example, any one of the patterns is selected as the drive channel pattern from three types; pattern N, pattern A, and pattern B, according to the table of FIG. 6.

If a user is allowed to select and use any type of a probe with the probe-specific channel pitch, it is possible to accept an input of the specified channel pitch d from the user as one of imaging parameters in the step 42. It is alternatively possible that a relationship between the types of the ultrasound probe 100 being mountable and the channel pitch d of each type is shown in the form of a table, or the like, and it is stored in advance in the memory. Then, in the step 42, the user selects one type of the ultrasound probe 100, and the controller 106 reads from the table, the channel pitch d of the selected ultrasound probe 100, so as to select proper drive channel pattern from the table of FIG. 6 with the channel pitch d.

The controller 106 displays on the monitor 110, the drive channel pattern being read out, and information for the user that this pattern is the optimum for suppressing the grating lobe. If the user accepts this pattern, the process moves on to the step 44. In the step 83, it is further possible to configure such that the user is allowed to optionally select a drive channel pattern other than the optimum pattern displayed on the monitor 110, and in that case, the controller 106 uses the pattern selected by the user.

Since the steps 41 to 42 and 44 to 46 other than discussed above are the same as those in the first embodiment, tedious explanations will not be made. The device configuration is also the same as that of the first embodiment.

As described above, in the second embodiment, an optimum drive channel pattern for suppressing the grating lobe can be selected depending on the imaging parameter, and therefore, after the processing in the signal processor 107, it is possible to reduce the linear component that still remains after canceling out due to the grating lobe. Therefore, an artifact caused by the linear component that remains after canceling out can be reduced, thereby obtaining a THI image having a higher ratio of nonlinear component.

Generation of the grating lobe also depends on the factional bandwidth of the transmission pulse. By way of example, if CMUT (Capacitive micro-machined ultrasonic transducers) or a single-crystal piezoelectric material is used as the electroacoustic conversion element, it is possible to generate a transmission pulse of broader band than the case of an element employing PZT (Lead Zirconate Titanate) that is widely used. Since the broad band pulse becomes substantially a single pulse, a region of wave overlapping in a direction other than the main axis direction is reduced, and therefore, the grating lobe is less likely to originate. As a specific example, FIG. 5(B) illustrates a simulation result in the case where the fractional bandwidth of the transmission pulse was set to be 125%, and the other conditions were the same as those illustrated in FIG. 5(A). The plot 1905 indicates the case where all the channels were driven, the plot 1906 indicates the case using the drive channel pattern as shown in FIG. 3(B), and the plot 1907 indicates the case using the drive channel pattern as shown in FIG. 3(E). Comparing the plot 1902 as shown in FIG. 5(A) with the plot 1906 as shown in FIG. 5(B), it is found that the grating lobe was suppressed by using the broad band pulse having the fractional bandwidth of 125%, even though the selected driven chancel pattern set the drive channels alternately as shown in FIG. 3(B).

As discussed above, an appropriate drive channel pattern for suppressing the grating lobe varies depending on the fractional bandwidth of the transmission pulse. Therefore, it is possible to consider the bandwidth of the transmission pulse as a parameter upon obtaining an optimum drive channel pattern. Since the fractional bandwidth is associated with the wave number in the time region of the transmission waveform, substantially the same result may be produced if the wave number of the transmission pulse is set as the parameter. On this occasion, upon obtaining the table as shown in FIG. 6 in advance according to computation, or the like, a table is created including the fractional bandwidth or the wave number of the transmission pulse as the parameter, and it is configured such that in the step 42 of FIG. 7, the controller 106 accepts the bandwidth of the transmission pulse from the user.

Figure 8:
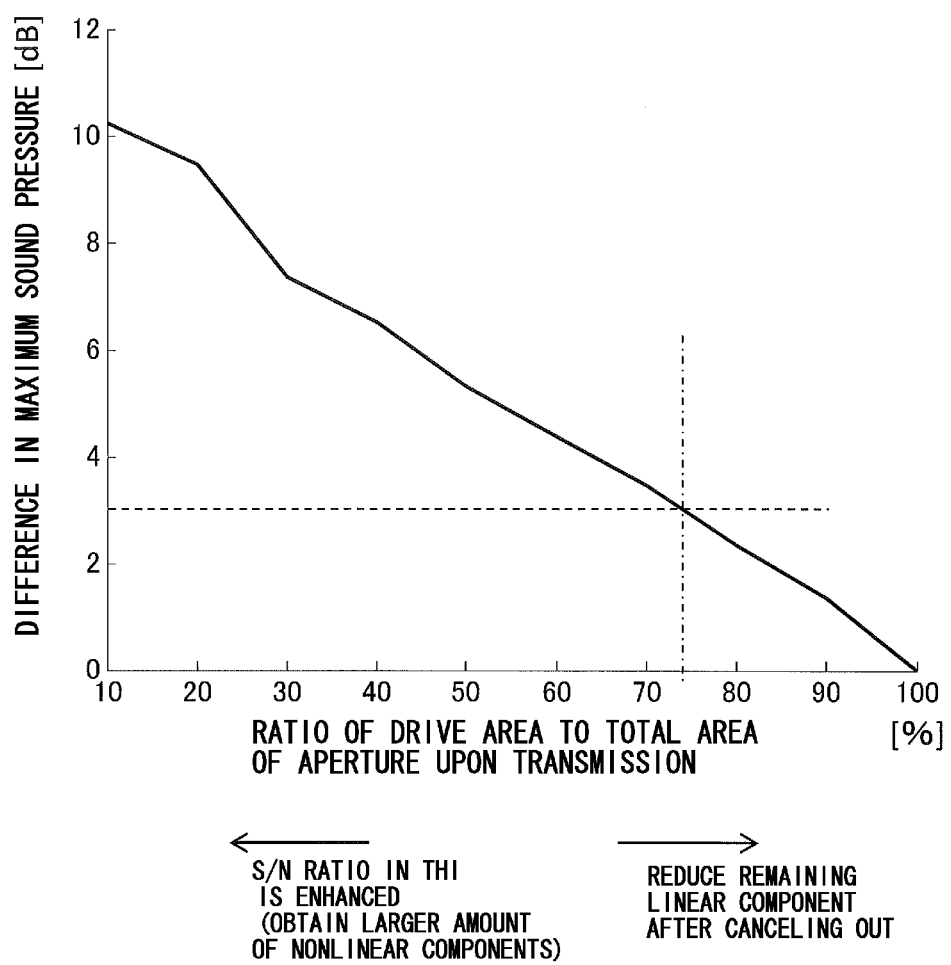
FIG. 8 is a graph showing a difference in maximum sound pressure between the case where all the channels within a transmission aperture are driven and the case where a part thereof is driven, along with changing a drive area in the second embodiment.

It is further possible to reduce the linear component residual after canceling out, not only by the drive channel pattern, but also by optimizing the ratio of the drive area. This will be explained with reference to the plot shown in FIG. 8. The horizontal axis of the plot represents a ratio of the drive channel area with respect to the total area of the aperture upon transmission, and the vertical axis represents a change of a maximum difference of sound pressure of the transmission beam when that drive area is used. The maximum difference of sound pressure indicates a sound pressure difference at the maximum point, among the differences compared to the overall transmission beam when all the channels within the transmission bore are driven. This plot was obtained from a result of the calculation using the simulation conditions that were similar to those of the plot 1903 in FIG. 5(A).

As the drive area upon transmission for the second transmission where the drive area is reduced becomes closer to the total area of the aperture upon transmission (becomes closer to 100%), the maximum sound pressure difference relative to the all-channel transmission (first transmission) becomes smaller. Therefore, the linear component residual after the computation on the received echo signals in the step 46 of FIG. 7 is reduced. Therefore, from the viewpoint of reducing the linear component residual after canceling out for suppressing an artifact, it is desirable that the drive area in the second transmission is close to the total area of the aperture upon transmission. On the other hand, the smaller drive area upon transmission for the second transmission results in a decrease of the sound pressure of the transmission beam. The nonlinear component generated in the echo signal for the second transmission thus becomes smaller. Therefore, it is possible to obtain a large amount of nonlinear component after the computation in the step 46 of FIG. 7, thereby achieving the THI with a high S/N ratio. Thus, in order to obtain a large amount of nonlinear component, it is desirable that the drive area in the second transmission is small.

In view of the situation above, the drive area is set within a range that achieves both reduction of the linear component after the canceling out, and increase of the nonlinear component. Specifically, if it is assumed that an amount of the artifact recognizable on the image, the artifact being caused by the linear component residual after canceling out, corresponds to the maximum sound pressure difference of 3 dB, it is desirable that the ratio of the drive area is equal to or higher than approximately 74% in the example of FIG. 8, from the view point of the reduction of linear component after canceling out. On the other hand, from the viewpoint of enhancing the S/N ratio, a smaller drive area is desirable in the second transmission. Considering both, the ratio of 74% is selected as the optimum drive area. Accordingly, it is possible to reduce the linear component residual after canceling out more favorably, while achieving the THI with a high S/N ratio.

Third Embodiment

An explanation will be made as to the ultrasonic diagnostic apparatus according to the third embodiment.

In the first and second embodiments, drive channels and non-drive channels are provided in the ultrasound probe 100 for one transmission out of transmission performed twice. Because the drive area (the number of driven electroacoustic conversion elements) thus reduce, the sound pressure of the transmission beam for the one transmission decrease. In the third embodiment, drive sub-channels and non-drive sub-channels are provided in units of sub-channel within the channel, and the sound pressure of the transmission beam is reduced.

Figure 9:
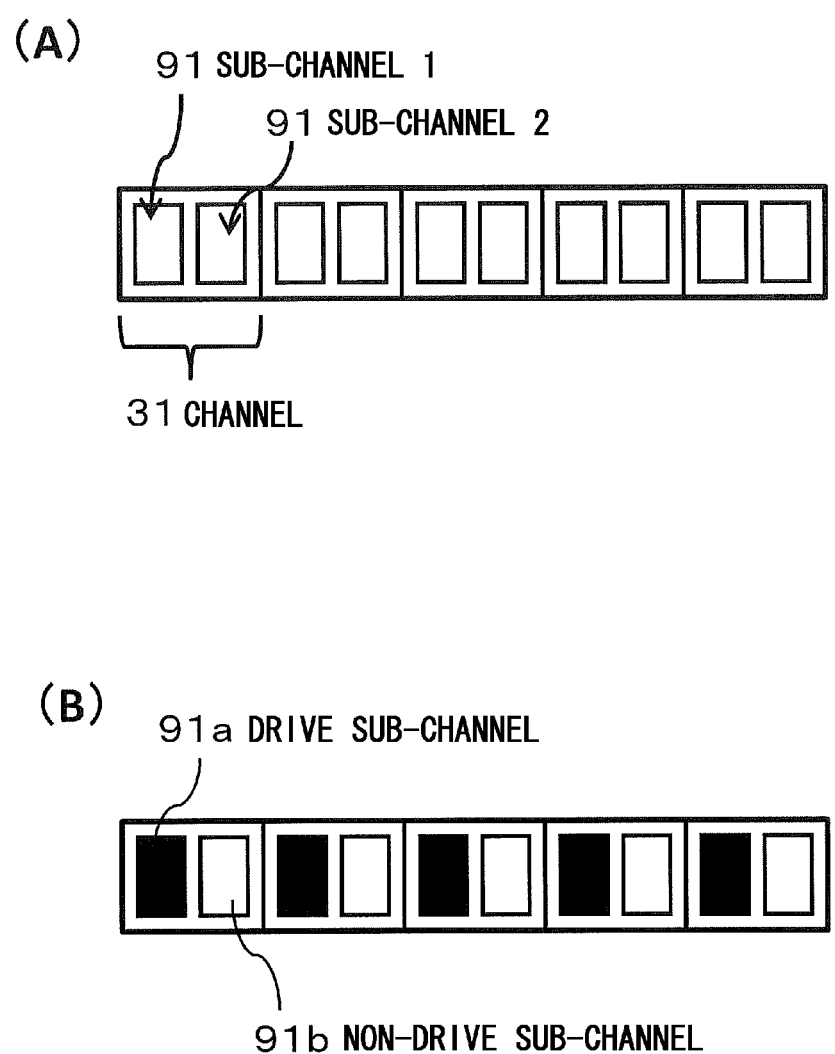
FIG. 9(A) illustrates a structure in which sub-channels are provided within a channel according to the third embodiment.
FIG. 9(B) illustrates a pattern of sub-channels being driven.

By way of example, as shown in FIG. 9(A), at least two sub-channels 91 are placed in each of the channels 31. Upon reducing the drive area, as shown in FIG. 9(B), only the sub-channel 91*a* is driven which is part of sub-channels 91 in each channel 31, and the residual sub-channel is set as the non-drive sub-channel 91*b*. With this configuration, according to the ratio of the sub-channels 91*a* being driven in the channels 31, the sound pressure of the transmission beam can be reduced. On this occasion, as shown in FIG. 9(B), if the distance between the drive sub-channels 91*a* is made constant within the aperture upon transmission of the ultrasound probe 100, it is sure that the pitch of the drive sub-channels 91*a* is equivalent to the pitch d of the channel 31. Even though the drive area is reduced, the pitch of the channel 31 is not expanded substantially. Therefore, the grating lobe is not generated due to expansion of the pitch.

Figure 10:
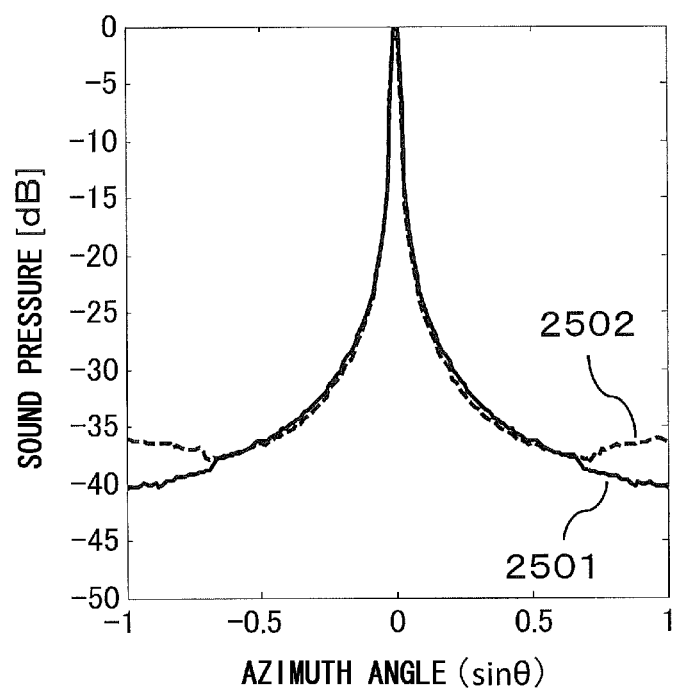
FIG. 10 is a graph showing a sound pressure distribution of a linear component of the ultrasound beam in the case of being driven in units of sub-channel according to the third embodiment.

FIG. 10 shows a linear-component acoustic field of the transmission beam in proximity to a focus depth of 20 mm obtained by simulation where a linear-array probe was used as the ultrasound probe 100. In the simulation, it was assumed that the sound velocity in the living body was 1,500 m/s, and the attenuation coefficient was 0.5 dB/cm/MHz. It was also assumed that the channel pitch d was 0.2 mm, being made up of 42 channels in total, and the transmission bore was approximately 8.4 mm. The center frequency of the transmission pulse was 9 MHz and the fractional bandwidth was 70%. The vertical axis of the graph in FIG. 10 represents the sound pressure, and the horizontal axis represents the angle in the azimuth direction indicated by sine function, and the main axis of the transmission beam was in the direction of $\sin \theta = 0$.

In FIG. 10, the plot 2501 represents a sound pressure distribution of the transmission beam in the case where all the sub-channels of all the channels 31 were driven, and the plot 2502 represents the case that one sub-channel 91*a* of the two sub-channels 91 constituting each channel was driven, thereby reducing the drive area to half. It is to be noted that both the plot 2501 and the plot 2502 were normalized at the maximum sound pressure, respectively.

As obvious from FIG. 10, the sound pressure distribution of the transmission beam represented by the plot 2502 approximately coincides with the sound pressure distribution of the transmission beam represented by the plot 2501, and it is found that generation of the grating lobe is curbed. As thus described, the drive sub-channel 91*a* and the non-drive sub-channel 91*b* are set in units of sub-channel constituting the channel 31. There is only a small difference in the acoustic field between those two plots. Therefore, even though the drive area is reduced, it is possible to curb the grating lobe and reduce the artifact caused by the linear component residual after canceling out.

It is to be noted that in order to set the drive sub-channel 91*a* and the non-drive sub-channel 91*b* in units of sub-channel within the channel 31, it is configured such that a switch is provided with respect to each channel 31 within the transmit-receive switch 101. For instance, as shown in FIG. 11(A), the switch 2402 performs switching to deliver a transmission signal from the transmission beam former 104 to the drive sub-channel 91*a*. The transmit-receive switch 101 performs the switching operation on the switch 2402 under the control by the controller 106.

Figure 12:
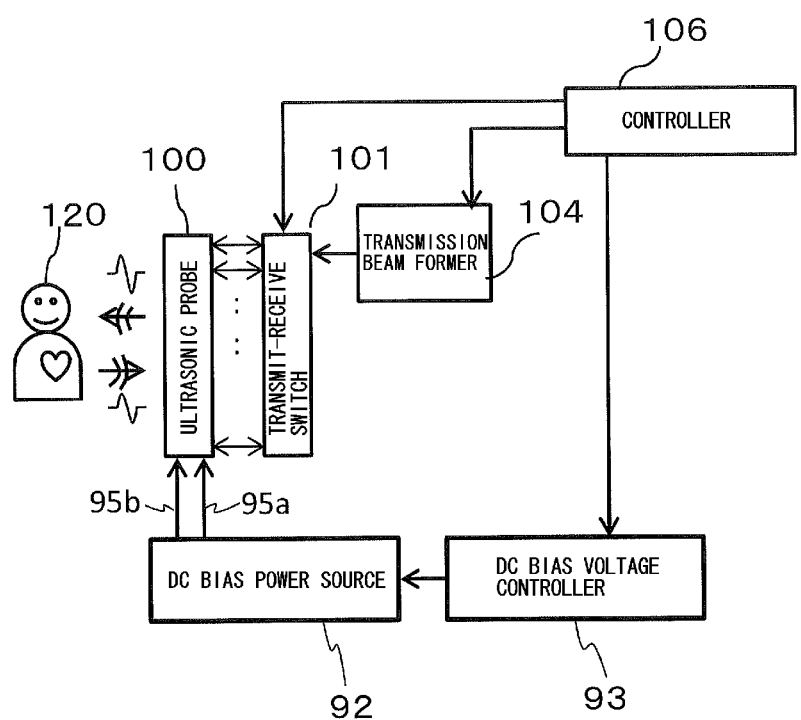
FIG. 12 is a block diagram illustrating a structure for implementing the sub-channels by CMUT according to the third embodiment.

In addition, if a capacitive transducer such as the CMUT is employed as the electroacoustic conversion element of the ultrasound probe 100, DC bias and AC voltage are applied between two electrodes placed on a vibrating membrane and within a lower substrate, thereby generating a difference in potential between electrodes and causing the vibrating membrane to vibrate. In the CMUT, if no bias voltage is applied, electroacoustic conversion efficiency is extremely low, and vibration occurs at a frequency twice as high as the frequency of AC voltage. Therefore, an effective transmission in a band of interest becomes impossible. Accordingly, the ultrasound probe 100 is connected to a power source 92 which supplies DC bias to one of the electrodes in each electroacoustic conversion element (CMUT), and the DC bias power source 92 is connected to a controller 93 for controlling the DC bias voltage as shown in FIG. 12. The transmission beam former 104 supplies AC voltage to each of the channels as a transmission signal.

Here, in the ultrasound probe 100 employing the CMUT, if sub-channels are provided in each channel, as shown in FIG. 11(A), it is possible to configure such that the AC voltage is delivered only to the CMUT of the drive sub-channel 91*a*, according to the switch 2402. It is further possible to configure as shown in FIG. 11(B) such that the DC bias is supplied only to the CMUT of the drive sub-channel 91*a*, and no DC bias is supplied to the non-drive sub-channel 91*b*. In the configuration as shown in FIG. 11(B), the DC bias is constant (common voltage) in the channel being driven. Therefore, it is only required to install DC bias systems 95*a* and 95*b*, the number of which is equal to the number of the sub-channels placed in one channel, and DC bias is applied from the system 95*a* to drive the drive sub-channel 91*a*, and no DC bias is applied from the system 95*b* to the non-drive sub-channel 91*b*. Upon driving all the sub-channels, the DC bias is supplied from all the systems 95*a* and 95*b*. With the configuration above, it is not necessary to provide switches the number of which corresponds to the number of channels, simplifying the configuration such that switches whose number is equal to the number of bias systems are provided in the DC bias power source 92 (in FIG. 11(B), the number of systems is two).

It is to be noted that FIG. 11(A) and FIG. 11(B) illustrate examples that two sub-channels are placed for one channel, but it is further possible to provide at least three sub-channels to make the drive area much smaller.

It is further possible to perform reduction of the drive area in units of sub-channel according to the present embodiment in combination with reduction of the drive area in units of channel as described in the first and the second embodiments.

Fourth Embodiment

The fourth embodiment is directed to an alternative example for suppressing the linear component residual after canceling out, caused by the grating lobe as described in the second and the third embodiments.

Figure 13:
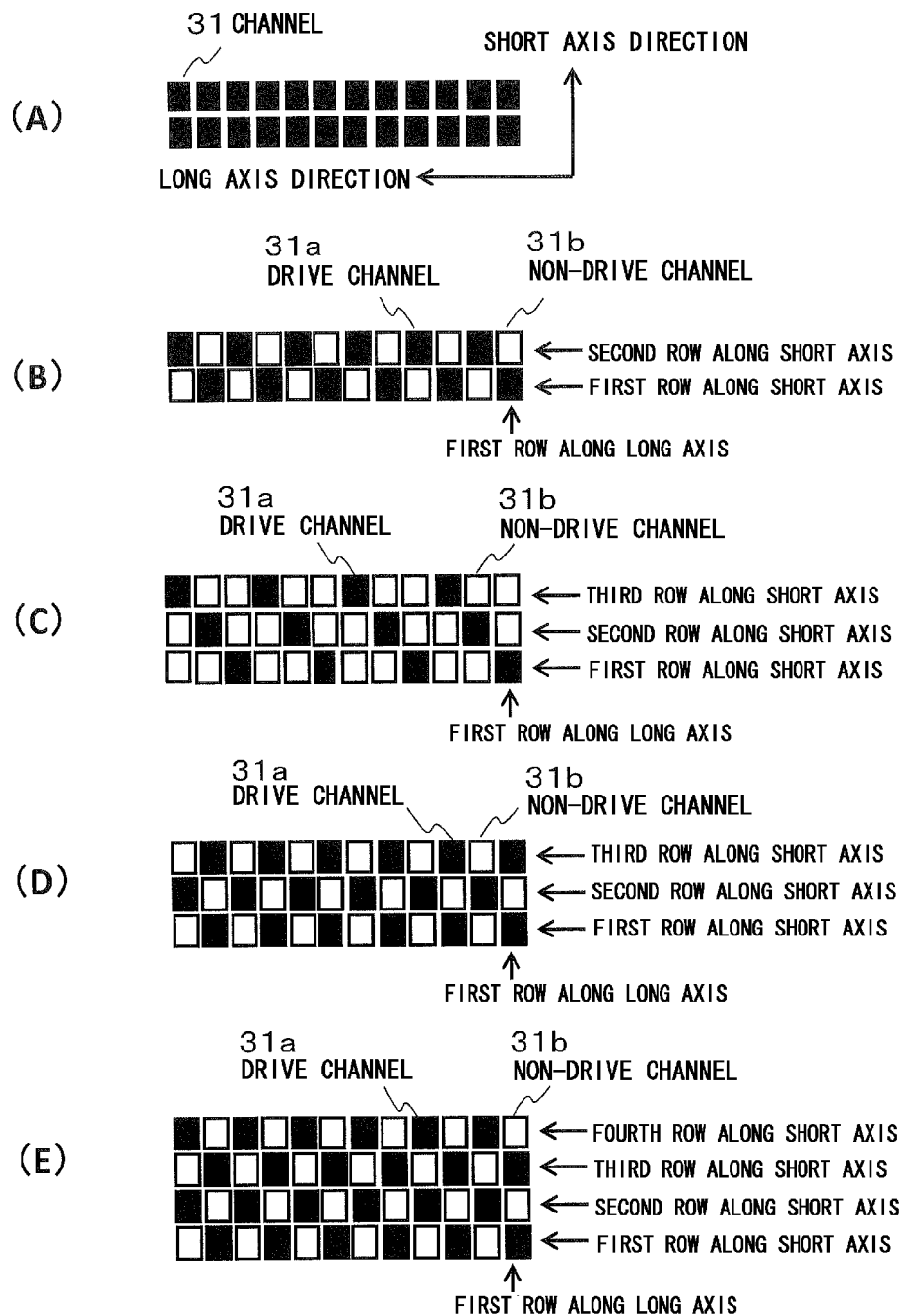
FIG. 13(A) to FIG. 13(E) illustrate drive channel patterns in the case where the channels are arranged two dimensionally according to the fourth embodiment.

Generally, an array-type ultrasound probe 100 such as a linear type and a convex type has an array structure of the electroacoustic conversion elements formed in a shape of rectangular. Multiple channels are placed in the form of array in the direction of the transmission bore (long axis), and a tomographic image of an imaging target is depicted in the long axis direction. In some cases, multiple channels are placed in the form of array also in the short axis direction that is orthogonal to the transmission bore. By way of example, as shown in FIG. 13(A), if the channels 31 are arranged two-dimensionally, a focus point of the ultrasound beam (transmission beam) is made by operating the delay time of the channels in the long axis direction. As for the channels in the short axis direction, there are several ways to make the focus point: a fixed focus point is made by an acoustic lens: the focus point is changed by changing the number of the drive channels in the short axis direction depending on the depth of the focus point.

As thus described, upon using the probe 100 in which channels are arranged not only in the long axis direction but also in the short axis direction, it is possible to suppress a grating lobe when the sound pressure of the transmission beam is reduced in one transmission out of the transmission performed twice as follows. If patterns of the drive channels 31*a* in the first row in the short axis direction are set as shown in FIG. 13(B) and FIG. 13(C), the drive channels 31*a* in rows after the first row (second row, third row, . . . etc) are set in such a manner as being mutually exclusive with the drive channels 31*a* in the first row. In other words, the drive channels 31*a* in rows after the first row are set different position from those in the first row in the short axis. On this occasion, a ratio of the area occupied by the drive channels in each row may be constant, or may be different row by row.

By arranging the drive channels 31*a* as described above, the drive area of the drive channel pattern as shown in FIG. 13(B) is ½ of the total area of the transmission aperture. However, as for the long axis direction, in the first row in the short axis and in the second row of in the short axis, the drive channels 31*a* are positioned in such a manner as compensating for the position of the non-drive channel each other. Therefore, in the long axis direction, the pitch of the drive channels 31*a* is substantially equivalent to the pitch when all the channels are driven. Therefore, as for the long axis direction, the acoustic field of the transmission beam being formed is equivalent to the acoustic field according to the beam forming with driving all the channels, and therefore, it is possible to curb generation of grating lobe in a tomographic image of the imaging target.

Similarly, the drive area of the drive channel pattern as shown in FIG. 13(C) is ⅓ of the total area of the transmission aperture. However, as for the long axis direction, the drive channels 31*a* in the first row, the second row, and the third row in the short axis are positioned in such a manner as compensating for one another. Therefore, as for the long axis direction, the pitch of the drive channels 31*a* is substantially equivalent to the pitch upon driving all the channels within the transmission aperture.

In the case to drive the channels where are arranged two dimensionally within the transmission aperture as shown in FIG. 13(B) and FIG. 13(C), it is possible to configure such that the transmission beam former 104 outputs the transmission signal to each of all the channels arranged two dimensionally. It is further possible to have a configuration for outputting the transmission signal only to the channels corresponding to one row along the long axis direction, and perform switching to deliver the transmission signal selectively to the channels in any of the first row, the second row, and the third row in the short axis, via the transmit-receive switch 101. Accordingly, it is possible to drive the channels 31*a* in the patterns as shown in FIG. 13(B) and FIG. 13(C).

In FIG. 13(C) as described above, an explanation has been made as to the drive channel pattern of the probe 100 where channels are arranged in three rows in the short axis direction, and the position of drive channels in each row in the short axis compensate for one another. However, as far as drive channels area of the long axis direction is formed a entire transmission aperture in the long axis being equivalent to the case where all the channels are driven, the drive channels in the short axis direction may be allowed to be driven as many times as required. By way of example, in the pattern as shown in FIG. 13(D), upon focusing on first row along the long axis, two channels are driven which are positioned in the first and third rows along the short axis. Even in this case, as for the long axis direction, the pitch of the drive channel 31*a* becomes substantially equivalent to the pitch upon driving all the channels within the transmission aperture, and therefore, it is possible to curve generation of the grating lobe. For this reason, if channels are placed in four or more rows in the short axis direction, a drive channel pattern may be configured in such a manner that the drive channel pattern of FIG. 13(B) or the drive channel pattern of FIG. 13(C) is repeatedly placed. By way of example, as shown in FIG. 13(E), in the case of a probe where channels are arranged in four rows in the short axis direction, it is possible to provide a pattern by arranging the drive channel pattern of FIG. 13(B) repeatedly twice in the short axis direction. In the case where the channels are arranged in six rows in the short axis direction, it is possible to form a pattern by arranging the drive channels of FIG. 13(C) repeatedly twice. It is further possible to form a pattern where the drive channel pattern of FIG. 13(B) and the drive channel pattern of FIG. 13(C) are alternately arranged in repeated manner in the short axis direction. In the case above, similar to the cases of FIG. 13(B) and FIG. 13(C), it is possible to obtain an effect to curb generation of the grating lobe. By arranging the patterns of FIG. 13(B) and FIG. 13(C) repeatedly as described above, even in the two-dimensional array ultrasound probe that can generate a transmission beam to the short axis direction as the long axis direction, generation of the grating lobe can be suppressed. Therefore, this is effective when tomographic images are obtained in multiple directions, by using the two-dimensional array ultrasound probe.

Since the configuration of the other transmission than the transmission with non-drive channel described above is the same as that of the first embodiment, tedious explanation will not be made. It is to be noted that by using the method for driving sub-channels described in the third embodiment, the present embodiment may be combined with the method for reducing the drive area in units of sub-channel.

Fifth Embodiment

In the fifth embodiment, as further alternative embodiment for avoiding the grating lobe, there will be explained a configuration that a frequency of an echo signal is selected according to a filter processor 132 of the signal processor 107. In other words, filtering is performed so as to acquire only the nonlinear signal in a low-frequency region, thereby avoiding the grating lobe.

Figure 14:
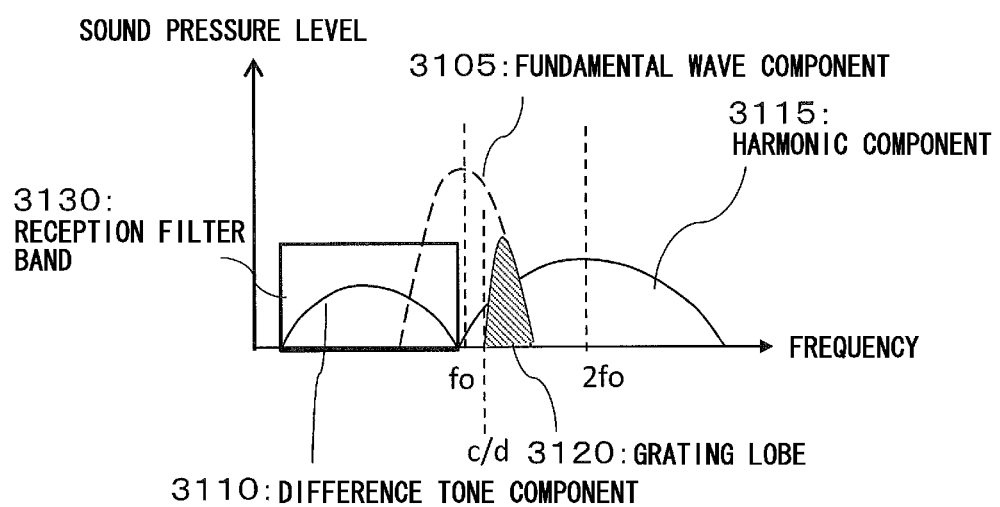
FIG. 14 illustrates a frequency band of the filter according to the fifth embodiment.

As shown in FIG. 14, when a pulse with a center frequency $f_0$ and a bandwidth 2fs is transmitted, a nonlinear component (difference frequency component) 3110 which is centered at fs, 2fs, or the like in the low-frequency region is generated during the propagation in the living body, in addition to a second higher harmonic component 3115 centered at $2f_0$.

On the other hand, when the main axis is vertical with respect to the bore as the case of a linear type probe, a condition for generating the grating lobe is $0<(\lambda/d)<1$, when it is assumed that a substantial channel pitch is d, and a wavelength of the ultrasound wave is $\lambda$. When the sound velocity is represented as c, and the frequency is represented as f, it is possible to rewrite $\lambda$ as $\lambda=c/f$. As shown in FIG. 14, the frequency region where the grating lobe 3120 is generated is expressed by f>c/d. By way of example, if a transmission beam is generated from the probe having the substantial channel pitch 0.4 mm, using the drive channel pattern as shown in FIG. 3(B), a grating lobe component being generated may appear in the frequency region being equal to or higher than 3.9 MHz.

In the present embodiment, by the use of these characteristics above, the grating lobe 3120 is removed. In other words, in the step 46 of FIG. 4, upon applying a receive filtering to cut a high-frequency wave, the filter processor 132 of the signal processor 107 sets a low-pass filter with cutoff value to be lower than c/d which is the lower limit of the frequency region of a grating lobe component, and removes the grating lobe. Accordingly, it is possible to prevent that the linear signal caused by the grating lobe 3120 remains in the reception signal, and extract a nonlinear signal in the difference frequency component 3110 generated in the low-frequency region. It is to be noted that in a scanning type probe for obtaining a wide field of view at a deep part by tilting the main axis, such as a sector type probe, a frequency range for generating the grating lobe may expand. Therefore, the substantial channel pitch d must be obtained from the physical channel pitch of the probe 100 and the drive channel pattern, and a cutoff frequency is then determined based on thus obtained d and the condition for generating the grating lobe.

Further explanations will be made, taking a specific example. Here, following case is considered; in the linear probe 100 having a structure with the physical channel pitch 0.2 mm, in the first transmission, all the channels within the transmission aperture are driven, and in the second transmission, only a half of the channels within the transmission aperture are driven. In the second transmission, the drive channel pattern as shown in FIG. 3(B) is employed. On this occasion, in the second transmission, the substantial pitch of the drive channel 31a is 0.4 mm. Therefore, if an ultrasound wave having the center frequency being 9 MHz is transmitted, a grating lobe occurs, but a region where the grating lobe appears corresponds to the frequency region being approximately 3.9 MHz or higher. Therefore, as for the echo signals in the transmission performed twice, the filter processor 132 of the signal processor 109 applies filtering to the signals in the step 46, by the receive filter which is set at a region lower than 3.9 MHz, and a computing process is carried out for extracting the nonlinear signal of the difference frequency component 3110.

The steps other than the discussed above are the same as those of the first embodiment shown in FIG. 4. In addition, the overall configuration of the apparatus is the same as that of the first embodiment.

As thus described, in the present embodiment, the grating lobe is removed by the filtering process and a nonlinear signal (difference frequency component) can be extracted. Therefore, it is possible to obtain a THI image based on the difference frequency component in which an artifact due to the grating lobe is suppressed.

Not only the first embodiment, but also the second or the third embodiment may be combined with the filtering process according to the present embodiment.

Sixth Embodiment

The ultrasonic diagnostic apparatus of the sixth embodiment will be explained. In the second to the fifth embodiments, it has been explained that a method for implementing the THI in the amplitude modulation method performing transmission twice. This method is not influenced by device nonlinearity, with suppressing the grating lobe and reducing a residual linear component after computation to cancel out. In the sixth embodiment, there will be explained an imaging method in which the transmission and reception are performed at least three times to completely remove the influence of the grating lobe.

In the present embodiment, upon the first transmission, all the channels within the aperture upon transmission of the ultrasound probe 100 are driven. Upon the transmissions from the second to the k-th (here, k≥3 and k is integer), the channels that is less than that of the first transmission are driven. On this occasion, the drive area (position of drive channels) upon the second to the k-th transmissions are determined in such a manner that a total region obtained by combining the drive areas (positions of drive channels), from the second to the k-th transmissions, coincide with the drive region upon the first transmission (all the channels within the transmission aperture). In other words, the drive channels from the second to the k-th transmissions are arranged in such a manner as being mutually exclusive with one another.

The linear component in the echo signal of the transmitted ultrasound wave is generated in proportion to the sound pressure of the transmission beam. Un amount of the linear component in the echo signals of the second to the k-th transmissions having the drive area of 1/n (n>1) the drive area upon the first transmission becomes 1/n of that in the echo signal of the first transmission. In addition, the total area obtained by combining the drive areas upon the second to the k-th transmissions coincides with the drive area upon the first transmission, and therefore, theoretically, the combined total of the linear components in the ultrasound beams of the second to the k-th transmissions completely coincides with that of the linear component in the ultrasound beam of the first transmission. Therefore, a computation such as combining the reception signals of all obtained by the transmission from the second to the k-th, and subtracting the result from the reception signal obtained by the first transmission, the linear component in the reception signals is completely canceled out. Since the grating lobe is also a linear component, it is also completely removed.

On the other hand, a nonlinear component is generated in proportion to the square of the sound pressure of the transmission beam while the ultrasound wave is propagating through the living body. Therefore, an amount of the nonlinear component in the echo signals from the second to the k-th transmissions having the drive area being 1/n (n>1) of the drive area upon the first transmission becomes to be multiplied by $1/n^2$. In other words, a ratio of the nonlinear component to the linear component included in the echo signals upon the transmissions from the second to the k-th becomes smaller than that upon the first transmission, and therefore, even though the reception signals combining all obtained by the transmission from the second to the k-th, are subtracted from the reception signal obtained by the first transmission, the nonlinear component remains. Therefore, according to this amplitude modulation method, it is possible to extract the nonlinear component.

Figure 15:
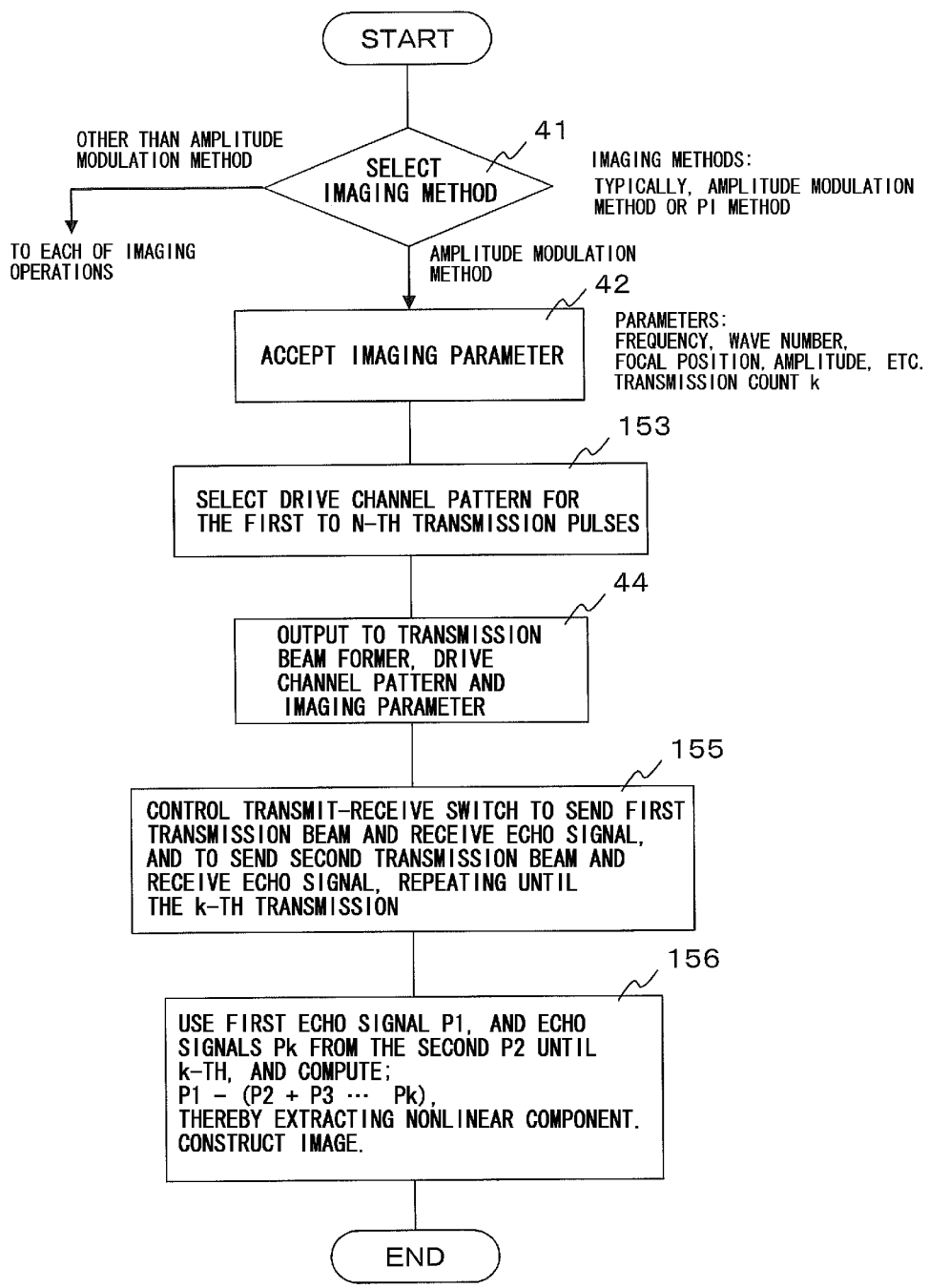
FIG. 15 is a flowchart showing a flow of the imaging operation according to the sixth embodiment.

As an operation for specific imaging, as shown in FIG. 15, an imaging method and imaging parameter are accepted from the user, similar to the steps 41 and 42 of the first embodiment as shown in FIG. 4. On this occasion, in the step 42, inputting of the transmission count k is accepted together with other parameters.

The memory built in the controller 106 stores in advance at least one drive channel pattern for each transmission count k being set. After setting the imaging parameter in the step 42, the controller 106 performs the step 153, and then reads the drive channel patterns in association with the transmission count k from the memory, displays the patterns on the monitor 110, and prompts the user to select a desired pattern from the drive channel patterns being displayed. When the user selects a pattern via the user interface 109, the controller 106 accepts this selection, and performs the process in the step 44 next. In the step 44, similar to the first embodiment, the controller 106 outputs the drive channel pattern and the imaging parameter to the transmission beam former 104.

In the next step 155, the controller drives the drive channels 31a in the drive channel pattern being set, transmits a transmission beam in each of the transmissions from the first to the k-th times, and receives an echo signal from each transmission. The signal processor 107 applies filtering process to the reception signals, and stores the signals in the memory 134. It is to be noted the aperture used in each of the transmissions and receptions is treated in the similar manner as the first embodiment.

In the step 156, the signal processor uses the reception signals from the first reception signal P1 to the k-th reception signal Pk, and performs the computation of P1−(P2+P3 . . . +Pk), thereby canceling out the linear component and extracting the nonlinear component. Thereafter, the image processor 108 constructs an image.

Accordingly, it is possible to obtain a THI image using the nonlinear signal with a high S/N ratio, from which the grating lobe as explained in the sixth embodiment is completely eliminated.

FIG. 16(A) to FIG. 16(F) illustrate examples of the drive channel pattern upon performing the transmission and reception three times (k=3). FIG. 16(A) illustrates the drive channel pattern that drive channels in the second and third transmissions are arranged alternately one by one. FIG. 16(B) and FIG. 16(C) illustrate that those drive channels are arranged alternately two by two, and three by three, respectively. FIG. 16(D) illustrates the case where an apparatus provided with a sub-channel structure as explained in the third embodiment is employed. In this pattern, two sub-channels are arranged in a channel, and the first sub-channel is driven as the drive sub-channel 91a in the second transmission, and the second sub-channel is driven as the drive sub-channel 91a in the third transmission. FIG. 16(E) illustrates a pattern in which channels positioned in the half-side region of the transmission aperture are set as the drive channels 31a in the second transmission, and channels positioned in the other side region of the transmission aperture are set as the drive channels 31a in the third transmission. FIG. 16(F) illustrates a pattern in which in the second transmission, channels in the outer region of the transmission aperture are set as the drive channels 31a, and in the third transmission, channels in the center region of the transmission aperture are set as the drive channels 31a.

FIG. 17(A) to FIG. 17(C) illustrate examples of the drive channel pattern upon performing the transmission five times (k=5). FIG. 17(D) illustrates an example of the pattern upon performing the transmission six times (k=6). FIG. 17(A) to FIG. 17(C) each illustrates the pattern for driving two channels in every transmission from the second to the fifth. FIG. 17(A) illustrates a pattern in which adjacent two channels are set as the drive channels 31a, and the positions thereof are displaced two by two in every transmission. FIG. 17(B) illustrates a pattern in which two channels positioned on both ends of the transmission aperture are set as the drive channels 31a, and then, drive channels are selected sequentially toward inside in every transmission. FIG. 17(C) illustrates a pattern in which two channels placing three channels therebetween are set as the drive channels 31a and the position of the drive channels are displaced in every transmission, while keeping the distance between the two drive channels 31a constant. FIG. 17(D) illustrates a pattern in which both the number and the positions of drive channels are assumed as random.

Figure 17:
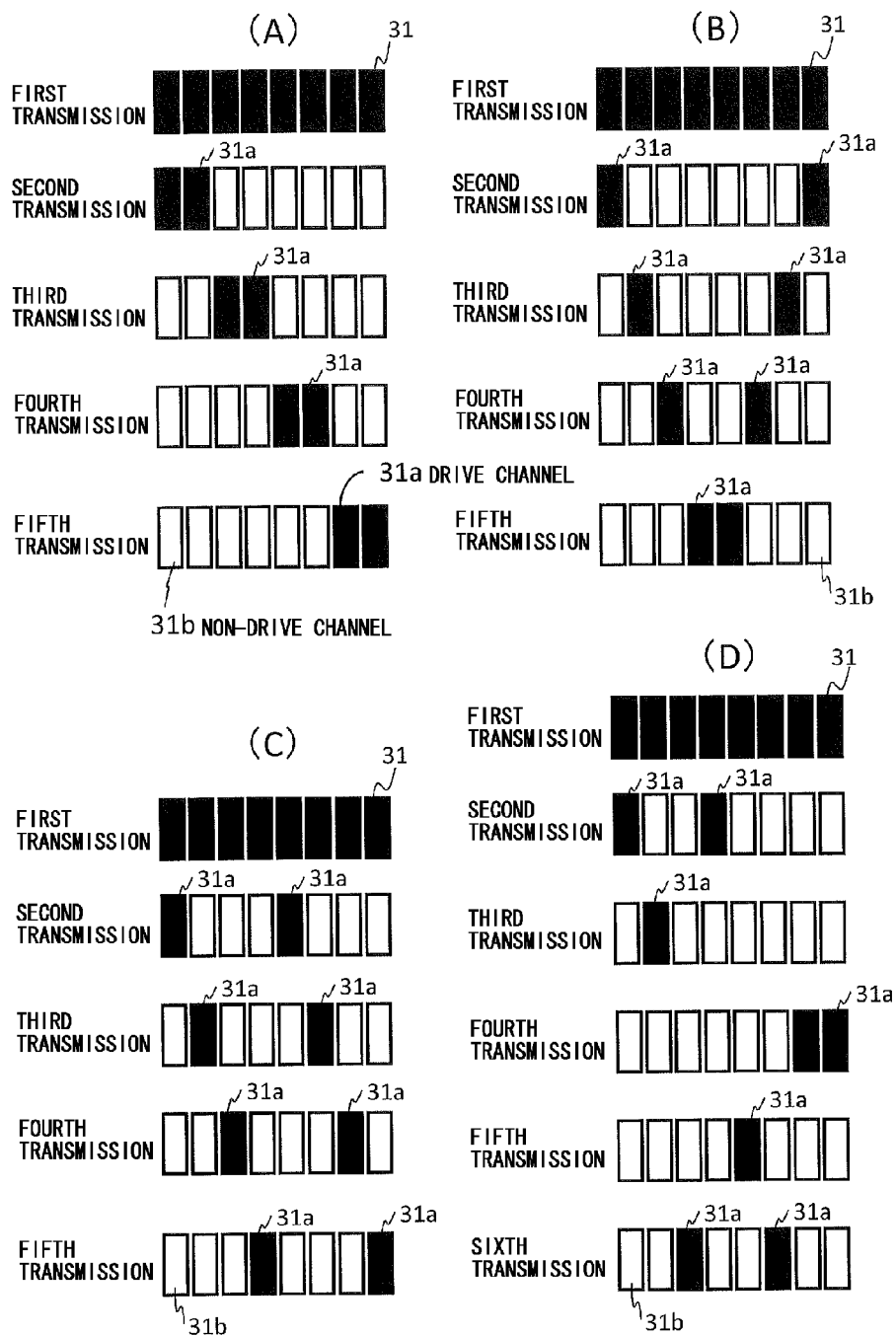
FIG. 17(A) to FIG. 17(D) each illustrates the drive channel pattern according to the sixth embodiment.

If any of the drive channels shown in FIG. 16 and FIG. 17 is used, upon combining the drive channels 31a from the second to the k-th transmissions, the combination is equivalent to the drive channels 31a of the first transmission. Therefore, a combined result of the linear acoustic fields of the echo signals received from the second to the k-th transmissions completely coincides with the linear acoustic field of the echo signal received in the first transmission. Therefore, when a computation is carried out on the reception signals to subtract the combined result (P2+P3 . . . +Pk) of all the echo signals received from the second to the k-th transmissions in the step 156, from the echo signal (P1) obtained by the first transmission, the linear component is completely canceled out, and only the nonlinear signal remains.

In the case of FIG. 17(A), if the amount of the nonlinear component of the echo signal P1 in the first transmission is assumed as $\alpha P^2$, an amount of the nonlinear components of the echo signal in each of the second to the fifth transmissions becomes $\alpha(1/16)P^2$, because each of the second to the fifth transmissions uses $1/4$ of the drive area in the first transmission. Thus, in the step 156 when the computation (P1−(P2+P3 . . . +Pk) for canceling out the linear component is carried out, extracted nonlinear component becomes $\alpha P^2 - 4 \times \alpha(1/16)P^2 = \alpha(3/4)P^2$.

In case of N times transmission (k=N), the drive area of each transmission is represented as 1/(N−1) of the total area of the transmission aperture where the drive area of each of the second to the N-th transmissions is assumed to be constant. When the sound pressure of the echo signal in the first transmission is assumed as P, the echo signal of each of the second to the N-th transmissions is expressed as $(1/(N-1))P + \alpha(1/(N-1)^2)P^2$. Therefore, a total of the echo signals from the second to the N-th transmissions is expressed as $P + \alpha(1/(N-1))P^2$, by multiplying the formula above by (N−1). When it is subtracted from the echo signal $(P + \alpha P^2)$ for the first transmission, the nonlinear component being obtained is expressed as $\alpha P^2(1 - 1/(N-1))$. In other words, the larger is the transmission count N (=k), the larger is the nonlinear signal obtained after the computing process.

Therefore, if a large amount of nonlinear signals are needed, it is desirable to set the total transmission count k to be a large number. If a high frame rate is prioritized, the case of k=3 is desirable. It is to be noted that in the case of the transmission performed three times, it is desirable that the drive area of the second transmission is set to be equal to the drive area of the third transmission since the nonlinear signal obtained after the computing process becomes large.

In order to extract a large amount of nonlinear signals according to the computing process, it is desirable to make the nonlinear signals included in the echo signals from the second to the k-th transmissions much smaller. This is because upon the computing process in the step 156, the echo signals from the second to the k-th transmissions are subtracted from the echo signal in the first transmission, and therefore the computing process reduces the nonlinear signals in the echo signals in the first transmission. In view of this, it is desirable to configure the pattern of the drive channels from the second to the k-th transmissions as a pattern that renders the amount of nonlinear signals as small as possible. In other words, an drive channel pattern that disperses the sound source is preferable, and it is also preferable that there is no imbalance in the drive channel pattern within the transmission aperture from the second to the k-th transmissions. By way of example, in the patterns of the transmission performed three times as illustrated in FIG. 16(A) to FIG. 16(F), the patterns illustrated in FIG. 16(A) and FIG. 16(D) are desirable because those patterns satisfy the condition above.

It is also possible to combine with the present embodiment by using the method for changing the drive area by driving the sub-channels as indicated in the third embodiment. It is further possible to combine the channels in the short axis direction as shown in the fourth embodiment, with the drive channel pattern.

In above examples, all the channels within the aperture upon transmission are driven by the first transmission, and a part of the channels within the aperture upon transmission is driven from the second to the k-th transmissions. The transmission for driving all the channels may be performed by any transmission among the first to the k-th transmissions. On this occasion, transmissions with driving a part of the channels are performed in the remaining transmissions.

Seventh Embodiment

In each of the first to the sixth embodiments, the imaging method for performing the THI has been explained. It is further possible to configure an ultrasonic diagnostic apparatus in which the imaging methods according to the first to the sixth embodiments can be executed selectively. This example is desirable because it allows a selection of an optimum method being required under the condition actually used.

By way of example, for the case where an imaging with high frame rate, it may be configured in such a manner as selecting automatically or manually, between the imaging method according to any of the first to the fifth embodiments that enable the THI by performing only the transmission twice. For the case where an imaging with high resolution is necessary, the imaging method according to the sixth embodiment may be selected.

EXPLANATION OF REFERENCES

100 ULTRASOUND PROBE
101 TRANSMIT-RECEIVE SWITCH
104 TRANSMISSION BEAM FORMER
105 RECEPTION BEAM FORMER
106 CONTROLLER
107 SIGNAL PROCESSOR
108 IMAGE PROCESSOR
109 USER INTERFACE
110 MONITOR
120 IMAGING TARGET
132 FILTER PROCESSOR
133 COMPUTING PROCESSOR
134 MEMORY
130 WAVEFORM SELECTION PART
131 TRANSMISSION WAVEFORM FORMER AND GENERATOR
1101 FIRST TRANSMISSION PULSE
1102 SECOND TRANSMISSION PULSE
1111 ECHO SIGNAL OF THE FIRST TRANSMISSION
1112 ECHO SIGNAL OF THE SECOND TRANSMISSION
1120 ECHO SIGNAL AFTER COMPUTING
1201 FIRST TRANSMISSION PULSE
1202 SECOND TRANSMISSION PULSE
1211 ECHO SIGNAL OF THE FIRST TRANSMISSION
1212 ECHO SIGNAL OF THE SECOND TRANSMISSION
1220 ECHO SIGNAL AFTER COMPUTING

What is claimed is:
1. An ultrasound imaging apparatus, comprising:
a transmitter which delivers a transmission signal to electroacoustic conversion elements in a transmit aperture having a predetermined area in multiple electroacoustic conversion elements arranged in a predeter- mined ultrasound transmit-receive surface and drives the electroacoustic conversion elements, and transmits an ultrasound beam to a predetermined position in an imaging target;

a receiver which instructs the multiple electroacoustic conversion elements in a predetermined receive aperture to receive an echo of the ultrasound beam from the imaging target, to obtain a reception signal;

a signal processor which subjects the reception signal to a computing process and generates an image; and a controller comprising a computer readable medium with a program disposed thereon, the program configured to instruct the transmitter to perform a first transmission to transmit a first ultrasound beam to a position in the imaging target and then instructs the receiver to perform a first reception to receive an echo of the first ultrasound beam, which thereafter instructs the transmitter to perform a second transmission to transmit a second ultrasound beam to a same position as the position being transmitted the first ultrasound beam and then instructs the receiver to perform a second reception to receive an echo of the second ultrasound beam, thereafter instructs the signal processor to perform computation on reception signals being obtained in the first reception and the second reception, thereby extracts a nonlinear component included in the reception signals, wherein, a transmit aperture in the second transmission is same as a transmit aperture in the first transmission, in one of the first transmission and the second transmission, the program disposed on the computer readable medium of the controller is further configured to instruct the transmitter to deliver the transmission signal to all of the electroacoustic conversion elements in the transmit aperture, and to drive the electroacoustic conversion elements, in another of the first transmission and the second transmission, the program disposed on the computer readable medium of the controller is further configured to instruct the transmitter to deliver the transmission signal selectively only to a part of the electroacoustic conversion elements in the transmit aperture, and to drive the electroacoustic conversion elements, a receive aperture in the second reception is same as a receive aperture in the first reception, and in the first reception and the second reception, the program disposed on the computer readable medium of the controller is further configured to instruct a plurality of identical electroacoustic conversion elements in the receive aperture to receive the echo of the first ultrasound beam and the echo of the second ultrasound beam, and to obtain reception signals.

2. The ultrasound imaging apparatus of claim 1, wherein a waveform of the transmission signal delivered to the part of the electroacoustic conversion elements in the another of the first transmission and the second transmission, is same as a waveform of the transmission signal delivered to the electroacoustic conversion elements in the one of the first transmission and the second transmission.

3. The ultrasound imaging apparatus of claim 1, wherein the multiple electroacoustic conversion elements are divided into multiple channels, in the another of the first transmission and the second transmission, the electroacoustic conversion elements to which the transmission signal is delivered and driven are selected in units of the channel.

4. The ultrasound imaging apparatus of claim 3, wherein, the channels are arranged two-dimensionally in a predetermined long axis direction and short axis direction, and the channels driven in each row along the long axis direction are arranged at positions being mutually exclusive between the rows.

5. The ultrasound imaging apparatus according to claim 3, wherein, the signal processor configured to perform a filtering process to extract the reception signal in a predetermined frequency band, the predetermined frequency band is equal to c/d or less, when distance between the multiple channels being driven is assumed as d, and sound velocity within the imaging target is assumed as c.

6. The ultrasound imaging apparatus of claim 3, wherein in the another of the first transmission and the second transmission, the controller delivers the transmission signal sequentially to adjacent channels.

7. The ultrasound imaging apparatus of claim 1, wherein the program disposed on the computer readable medium of the controller is further configured to instruct selecting the electroacoustic conversion elements to which the transmission signal is delivered in the another of the first transmission and the second transmission, according to a pattern of the electroacoustic conversion elements to be driven, the pattern being predetermined in association with an imaging parameter.

8. The ultrasound imaging apparatus of claim 7, further comprising a user interface for accepting an input of the imaging parameter from an operator, wherein the program disposed on the computer readable medium of the controller is further configured to instruct selecting the pattern corresponding to the imaging parameter accepted by the user interface.

9. The ultrasound imaging apparatus of claim 7, wherein the program disposed on the computer readable medium of the controller is further configured to instruct selecting the pattern for minimizing a grating lobe, in association with the imaging parameter.

10. The ultrasound imaging apparatus according to claim 9, wherein, the program disposed on the computer readable medium of the controller is further configured to instruct setting a filtering process for extracting the reception signal in a predetermined frequency region corresponding to the imaging parameter, in order to minimize the grating lobe.

11. The ultrasound imaging apparatus of claim 1, wherein the multiple electroacoustic conversion elements are divided into multiple channels, and each of the channels is further divided into multiple sub-channels, in the another of the first transmission and the second transmission, with respect to each channel, at least one sub-channel is selected from the multiple sub-channels, and the electroacoustic conversion elements in the sub-channels to which the transmission signal is delivered, and are driven.

12. The ultrasound imaging apparatus of claim 1, wherein, the multiple electroacoustic conversion elements are capacitance type electroacoustic conversion elements, are applied DC bias voltage and an AC voltage signal supplied from the transmitter as the transmission signal, the program disposed on the computer readable medium of the controller is further configured to instruct:
supplying the DC bias voltage only to the part of the electroacoustic conversion elements in the transmit aperture to which the transmission signal is delivered selectively in the another of the first transmission and the second transmission, and supplying no DC bias voltage to the other electroacoustic conversion elements.

13. An ultrasound imaging apparatus, comprising:
a transmitter which delivers a transmission signal to electroacoustic conversion elements in a transmit aperture having a predetermined ultrasound transmit-receive surface and drives the electroacoustic conversion elements, to transmit an ultrasound beam to a predetermined position in an imaging target;
a receiver which instructs the multiple electroacoustic conversion elements in a predetermined receive aperture to receive an echo of the ultrasound beam from the imaging target, to obtain a reception signal;
a signal processor which subjects the reception signal to a computing process and generates an image; and
a controller comprising a computer readable medium with a program disposed thereon, the program configured to instruct the transmitter and the receiver to perform a transmit-receive operation, wherein the transmitter transmits the ultrasound beam to an identical position of the imaging target and thereafter the receiver receives the echo of the ultrasound beam, repeatedly more than twice, wherein,
   ultrasound beams transmitted in the transmit-receive operation more than twice have different amplitude, and the signal processor computes on the reception signals being obtained in the transmit-receive operation more than twice to extract a nonlinear component included in the reception signals,
   the transmit apertures used in the transmit-receive operation more than twice are same,
   the program disposed on the computer readable medium of the controller is further configured to instruct the transmit-receive operation more than twice to include a transmission wherein all of the electroacoustic conversion elements in the transmit aperture are delivered as transmission signals and are driven, and a transmission wherein a part of the electroacoustic conversion elements in the transmit aperture are selectively delivered as transmission signals and are driven,
   the receive apertures used in the transmit-receive operation more than twice are same, and
   the program disposed on the computer readable medium of the controller is further configured to instruct a plurality of identical electroacoustic conversion elements in the receive aperture to receive each echo of the ultrasound beams in the transmit-receive operation more than twice, and to obtain reception signals.

14. An ultrasound imaging apparatus, comprising:
a transmitter which delivers a transmission signal to electroacoustic conversion elements in a transmit aperture having a predetermined area in multiple electroacoustic conversion elements arranged in a predetermined ultrasound transmit-receive surface and drives the electroacoustic conversion elements, to transmit an ultrasound beam to a predetermined position in an imaging target;
a receiver which instructs the multiple electroacoustic conversion elements in a predetermined receive aperture to receive an echo of the ultrasound beam from the imaging target, to obtain a reception signal;
a signal processor which subjects the reception signal to a computing process and generates an image; and
a controller comprising a computer readable medium with a program disposed thereon, the program configured to instruct the transmitter and the receiver to perform a transmit-receive operation, wherein the transmitter transmits the ultrasound beam to an identical position of the imaging target, and thereafter the receiver receives the echo of the ultrasound beam, repeatedly more than three times,
wherein,
   the signal processor computes on the reception signals being obtained in every reception in the transmit-receive operation more than three times to extract a nonlinear component included in the reception signals,
   the transmit apertures used in the transmit-receive operation more than three times are same,
   the program disposed on the computer readable medium of the controller is further configured to instruct the transmit-receive operation more than three times to include one transmission where all of electroacoustic conversion elements in the transmit aperture are delivered as transmission signals and are driven, and other transmissions more than twice wherein only a part of electroacoustic conversion elements in the transmit aperture are selectively delivered as transmission signals and are driven,
   the conversion elements delivered the transmission signals in the other transmissions more than twice are selected in a mutually exclusive manner between each transmission, from a plurality of electroacoustic conversion elements in the transmit aperture,
   the receive apertures used in the transmit-receive operation more than three times are the same,
   the program disposed on the computer readable medium of the controller is further configured to instruct a plurality of identical electroacoustic conversion elements in the receive aperture to receive each echo of the ultrasound beams in the transmit-receive operation more than three times, and to obtain reception signals.

15. The ultrasound imaging apparatus of claim 14, wherein the signal processor subtracts all of the reception signals obtained in the other transmission more than twice, from the reception signals obtained in the one transmission, thereby extracts the nonlinear component included in the reception signal.

16. The ultrasound imaging apparatus of claim 14, wherein in the other transmission more than twice, each of all of the electroacoustic conversion elements in the transmit aperture is driven one time.

17. The ultrasound imaging apparatus of claim 14, wherein in each transmission of the other transmissions more than twice, the program disposed on the computer readable medium of the controller is further configured to instruct selecting the electroacoustic conversion elements to which the transmission signal is delivered for driving the electroacoustic conversion elements, in such a manner that an area formed by the electroacoustic conversion elements to which the transmissions signal is delivered for driving is constant in the other transmission more than twice.

18. The ultrasound imaging apparatus of claim 14, wherein the multiple electroacoustic conversion elements are divided into multiple channels,
   in the other transmission more than twice, the electroacoustic conversion elements to which the transmission signal is delivered and driven are selected in units of the channel.

19. The ultrasound imaging apparatus of claim 18, wherein,
- in the other transmission more than twice, the program disposed on the computer readable medium of the controller is further configured to instruct selecting alternately, at least one by one,
- a channel to which the transmission signal is delivered for driving, and
- a channel to which no transmission signal is delivered.

20. The ultrasound imaging apparatus of claim 14, wherein, the multiple electroacoustic conversion elements are divided into multiple channels, and each of the channels is further divided into multiple sub-channels,
- in the other transmission more than twice, the electroacoustic conversion elements to which the transmission signal is delivered and driven are selected in units of the sub-channel.

21. The ultrasound imaging apparatus of claim 20, wherein, in the other transmission more than twice, a sub-channel to which the transmission signal is delivered for driving and a sub-channel to which no transmission signal is delivered are selected from the multiple sub-channels, alternately at least one by one, with respect to each channel.

* * * * *